United States Patent [19]

Kunisch et al.

[11] Patent Number: 5,296,503
[45] Date of Patent: Mar. 22, 1994

[54] MEDICAMENTS CONTAINING SUBSTITUTED 2-CYCLOHEXENE DERIVATIVES AND THEIR USE FOR THE CONTROL OF CANDIDA INFECTIONS

[75] Inventors: Franz Kunisch, Odenthal-Glöbusch; Peter Babczinski, Wuppertal; Dieter Arlt, Cologne; Manfred Plempel, Haan, all of Fed. Rep. of Germany

[73] Assignee: Bayer Aktiengesellschaft, Leverkusen, Fed. Rep. of Germany

[21] Appl. No.: 62,486

[22] Filed: May 14, 1993

Related U.S. Application Data

[63] Continuation of Ser. No. 751,022, Jul. 28, 1991, abandoned.

[30] Foreign Application Priority Data

Sep. 5, 1990 [DE] Fed. Rep. of Germany ....... 4028046

[51] Int. Cl.$^5$ .................. A61K 31/215; A61K 31/13; A61K 31/045
[52] U.S. Cl. ................................. 514/529; 514/579; 514/729
[58] Field of Search ........................ 514/529, 579, 729

[56] References Cited

U.S. PATENT DOCUMENTS 3,882,164  5/1975  Satzinger et al. ............... 260/471 A
4,666,930  5/1987  Salzburg ............................. 514/373

FOREIGN PATENT DOCUMENTS 0258853  9/1988  European Pat. Off. .
0376072  7/1990  European Pat. Off. .
0445749  11/1991 European Pat. Off. .
2150516  9/1971  Fed. Rep. of Germany .
2243803  7/1972  Fed. Rep. of Germany .
3126818  1/1983  Fed. Rep. of Germany .
2014957  4/1970  France .

OTHER PUBLICATIONS

Journal of Medicinal Chemistry, vol. 24, No. 7, Jul. 1981, pp. 788–793.
J. Organ. Chem., 26, 3511, (1961).
Houben–Weyl, Methoden der Organischen Chemie, 4th Ed., E. Muller, Ed. vol. 5/1c, Georg Thieme Verlag, Stuttgart, 1970, 977 J. Chem. Soc. Perkin Trans. 1, 1557–62, (1981).
Some Modern Methods of Organic Synthesis, W. Carruthers, Cambridge University Press, 1986, p. 125.
Acc. Chem. Res., 146 (1979).
J. Med Chem., 29, 1–8, (1986).
J. Med. Chem., 24, 788–94, (1981).
J. Am. Chem. Soc., 103, 2816–22, (1981).
J. Am. Chem. Soc., 100, 3182–3189, (1978).
J. Am. Chem. Soc., 100, 5179–85, (1978).
Tetrahedron Lett. 25, 2183–2186, (1984).
J. Org. Chem., 46, 2833–2835, (1981).
J. Am. Chem. Soc., 105, 5373–5379, (1983).
J. Org. Chem., 43, 2164, (1978).
J. Org. Chem., 30, 2414, (1965).
J. Chem. Soc., 7285, (1965).
J. Med. Chem. 10, vol. 10, pp. 844–849 1962.

Primary Examiner—Frederick E. Waddell
Assistant Examiner—Gregory Hook
Attorney, Agent, or Firm—Sprung Horn Kramer & Woods

[57] ABSTRACT

The present invention relates to the use of known substituted 2-cyclohexene derivatives in the control of diseases, in particular bacterial infections and mycoses.

6 Claims, No Drawings

MEDICAMENTS CONTAINING SUBSTITUTED 2-CYCLOHEXENE DERIVATIVES AND THEIR USE FOR THE CONTROL OF CANDIDA INFECTIONS

This application is a continuation of application Ser. No. 751,022, filed Jul. 28, 1991, now abandoned.

The present invention relates to the use of known substituted 2-cyclohexene derivatives in the control of diseases, in particular bacterial infections and mycoses.

The compounds according to the invention are described in detail in European Patent Application EP 0,376,072 A2.

It has now been found that the substituted 2-cyclohexene derivates of the formula (I)

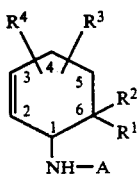

in which $R^1$ represents hydrogen, alkyl or halogen, $R^2$ represents formyl, hydroxyalkyl, cyano, nitro or one of the radicals

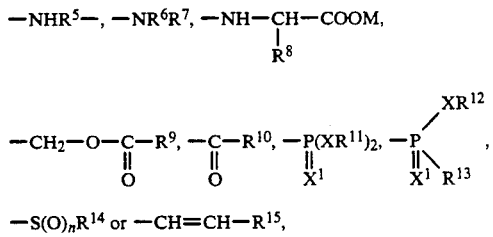

$-S(O)_nR^{14}$ or $-CH=CH-R^{15}$, $R^3$ and $R^4$ are identical or different and in each case represent hydrogen, alkyl, alkenyl, alkinyl, alkoxy, alkenyloxy, alkinyloxy, unsubstituted or substituted aryl, unsubstituted or substituted aralkyl, unsubstituted or substituted heteroaryl, unsubstituted or substituted heterocyclylalkyl, alkoxyalkyloxy, halogen or one of the radicals $-NH-R^5$, $-NR^6R^7$, or $-S(O)_n-R^{14}$ or or $R^2$ and $R^3$ together represent one of the radicals

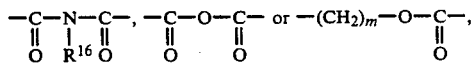

bridged via the positions 6 and 5, or $R^3$ and $R^4$ together represent an alkyl chain having 3 or 4 carbon atoms, which is bonded via the positions 4 and 3, $R^5$ represents hydrogen, alkyl or unsubstituted or substituted aryl, $R^6$ represents alkyl or unsubstituted or substituted aryl, $R^7$ represents alkyl or unsubstituted or substituted aryl, $R^8$ represents hydrogen, alkyl, unsubstituted or substituted aryl or unsubstituted or substituted aralkyl, $R^9$ represents alkyl or alkoxy, $R^{10}$ represents hydroxyl, hydroxyalkyloxy, halogenoalkyloxy, alkoxy, alkoxyalkyloxy, unsubstituted or substituted cycloalkyloxy, unsubstituted or substituted aralkyloxy, unsubstituted or substituted aryloxy, unsubstituted or substituted aralkyl, alkylthio, unsubstituted or substituted arylthio or a group $-OM$, $-NHR^5$, $-NR^6R^7$ or $-O-Z-NR^5R^6$, $R^{11}$ represents hydrogen or alkyl, $R^{12}$ represents hydrogen or alkyl, $R^{13}$ represents alkyl, $R^{14}$ represents alkyl, alkoxy, unsubstituted or substituted aryl or the group $-OM$, $R^{15}$ represents formyl, cyano or the group

$R^{16}$ represents hydrogen, alkyl or unsubstituted or substituted aryl,

M represents hydrogen or an equivalent of an appropriate alkali metal, alkaline earth metal or ammonium cation, n represents a number 0, 1 or 2, X and $X^1$ are identical or different and represent oxygen or sulphur, m represents a number 1 or 2, A represents hydrogen or an amino protecting group and Z represents a straight-chain or branched alkyl chain, and their acid addition salts and metal salt complexes have strong antimicrobial properties, in particular strong antibacterial and antimycotic properties.

The compounds of the formula (I) can be present as geometrical isomers (E/Z isomers) or isomer mixtures of different composition. The use both of the pure isomers and of the isomer mixtures are claimed according to the invention.

The compounds of the formula (I) additionally contain 1 to 4 centres of chirality and can thus exist in various enantiomeric and diastereomeric mixtures which, if desired, can be separated in a customary manner. The use both of the pure enantiomers and diastereomers and also that of the mixtures are likewise claimed according to the invention.

In the following, for the sake of simplicity, the use of compounds of the formula (I) is always referred to, although both the pure compounds and the mixtures containing different amounts of isomeric, enantiomeric and diastereomeric compounds are meant.

Formula (I) provides a general definition of the substituted 2-cyclohexen-1-yl-amine derivatives to be used according to the invention.

The terms in the general formulae have the meaning in the following, if not defined otherwise: alkyl - straight-chain or branched alkyl having 1 to 8, preferably 1 to 6, in particular 1 to 4 carbon atoms. Those which may be mentioned as examples and in preference are optionally substituted methyl, ethyl, n.- and i.-propyl, and n-, i-, s- and t-butyl.

Alkenyl and the alkenyl moiety of optionally substituted alkenyloxy - straight-chain or branched alkenyl having 2 to 8, preferably 2 to 6, in particular 2 to 4 carbon atoms. Those which may be mentioned as examples and in preference are optionally substituted ethenyl, prop-1-enyl, prop-2-enyl and but-3-enyl.

Alkinyl and the alkinyl moiety of optionally substituted alkinyloxy - straight-chain or branched alkinyl having 2 to 8, preferably 2 to 6, in particular 2 to 4 carbon atoms. Those which may be mentioned as examples and in preference are optionally substituted ethinyl, prop-1-inyl, prop-2-inyl and but-3-inyl.

Alkoxy - unsubstituted or substituted, straight-chain or branched alkoxy having 1 to 8, preferably 1 to 6, in particular 1 to 4 carbon atoms. Those which may be mentioned as examples and in preference are optionally substituted methoxy, ethoxy, n.- and i.-propoxy and n-, i-, s- and t-butoxy.

Aryl - preferably unsubstituted or substituted phenyl or naphthyl, in particular phenyl.

Aralkyl and aralkoxy aralkyl or aralkoxy which is unsubstituted or substituted in the aryl moiety and/or alkyl moiety, preferably having 6 or 10, in particular 6 carbon atoms in the aryl moiety (preferably phenyl or naphthyl, in particular phenyl) and preferably having 1 to 8, in particular 1 to 6 carbon atoms in the alkyl moiety, it being possible for the alkyl moiety to be straight-chain or branched. Those which may be mentioned as examples and in preference are optionally substituted benzyl and phenylethyl or benzyloxy and phenylethyloxy.

Unsubstituted or substituted heterocyclic radicals in the general formulae denote heteroparaffinic, heteroaromatic and heteroolefinic 5-6-membered rings preferably having 1 to 3, in particular 1 or 2 identical or different heteroatoms. Heteroatoms are oxygen, sulphur or nitrogen. Those which may be mentioned by way of example and in preference are pyrrolidinyl, piperidinyl, furyl, thienyl, pyrazolyl, imidazolyl, 1,2,3- and 1,2,4-triazolyl, oxazolyl, isoxazolyl thiazolyl, isothiazolyl, 1,3,4- and 1,2,4-oxadiazolyl, azepinyl, pyrrolyl, isopyrrolyl, pyridyl, pyridazinyl, pyrimidinyl, pyrazinyl and 1,2,3-, 1,2,4-, 1,2,5- and 1,3,4-thiadiazolyl.

Halogen in the general formulae preferably denotes fluorine, chlorine, bromine and iodine, in particular fluorine, chlorine and bromine and particularly preferably fluorine and chlorine.

The optionally substituted radicals of the general formulae can carry one or more, preferably 1 to 3, in particular 1 or 2 identical or different substituents. Substituents which may be mentioned by way of example and listed in preference are:

Alkyl preferably having 1 to 4, in particular 1 or 2 carbon atoms, such as methyl, ethyl, n.- and i.-propyl and n.-, i.- and t.-butyl; alkoxy preferably having 1 to 4, in particular 1 or 2 carbon atoms, such as methoxy, ethoxy, n.- and i.-propyloxy and n.-, i.-, sec.- and t.-butyloxy; alkylthio preferably having 1 to 4, in particular 1 or 2 carbon atoms, such as methylthio, ethylthio, n.- and i.-propylthio and n.-, i.-, sec.- and t.-butylthio; halogenoalkyl, halogenoalkoxy and halogenoalkylthio preferably having 1 to 4, in particular 1 or 2 carbon atoms and preferably 1 to 9, in particular 1 to 5 halogen atoms, the halogen atoms being identical or different and preferably being fluorine, chlorine or bromine, in particular fluorine, such as trifluoromethyl, trifluoromethoxy and trifluoromethylthio; hydroxyl; halogen, preferably fluorine, chlorine, bromine and iodine, in particular fluorine, chlorine and bromine; cyano; nitro; amino; dialkylamino preferably having 1 to 4, in particular 1 or 2 carbon atoms per alkyl group, such as methyl-ethyl-amino, and methyl-n.-butyl-amino; carboxyl.

Preferably used compounds of the formula (I) are those in which $R^1$ represents hydrogen, straight-chain or branched alkyl having 1 to 6 carbon atoms or fluorine, chlorine or bromine, $R^2$ represents formyl, straight-chain or branched hydroxyalkyl having 1 to 8 carbon atoms in the alkyl moiety, cyano, nitro or one of the radicals

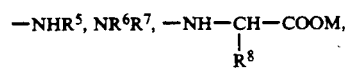

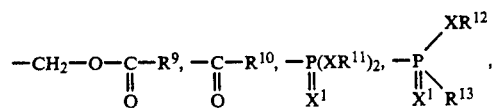

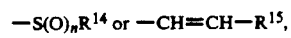

$R^3$ and $R^4$ are identical or different and in each case represent hydrogen, alkyl or alkoxy having 1 to 8 carbon atoms, which is in each case straight-chain or branched, alkenyl, alkinyl, alkenyloxy or alkinyloxy in each case having 2 to 8 carbon atoms, which is in each case straight-chain or branched, alkoxyalkyloxy in each case having 1 to 8 carbon atoms in the individual alkyl moieties, aryl or aralkyl in each case having 6 to 10 carbon atoms in the aryl moiety and optionally 1 to 4 carbon atoms in the alkyl moiety and in each case unsubstituted or monosubstituted to pentasubstituted in the aryl moiety by identical or different substituents, suitable aryl substituents being: halogen, nitro, cyano, amino, $C_1$–$C_4$-alkyl, $C_1$–$C_4$-alkoxy or $C_1$–$C_4$-alkylthio, halogeno-($C_1$–$C_4$)-alkyl, halogeno-($C_1$–$C_4$)-alkoxy, halogeno-($C_1$–$C_4$)-alkylthio in each case having 1 to 9 identical or different halogen atoms and di-(C -C )-alkylamino, furthermore a heterocyclic 5- or 6-membered ring which can contain 1 to 3 oxygen, sulphur and/or nitrogen atoms as further heteroatoms and is unsubstituted or monosubstituted to pentasubstituted by identical or different substituents, or heterocyclylalkyl having a 5- or 6-membered ring which can contain 1 to 3 oxygen, sulphur and/or nitrogen atoms as further heteroatoms and 1 or 2 carbon atoms in the alkyl moiety and is unsubstituted or monosubstituted to pentasubstituted by identical or different substituents, suitable substituents for the heterocycle in each case being: halogen, nitro, cyano, amino, $C_1$–$C_4$-alkyl, $C_1$–$C_4$-alkoxy or $C_1$–$C_4$-alkylthio, halogeno-($C_1$–$C_4$)-alkyl halogeno-($C_1$–$C_4$)-alkoxy or halogeno-($C_1$–$C_4$)-alkylthio in each case having 1 to 9 identical or different halogen atoms, and di-($C_1$–$C_4$)-alkylamino, furthermore fluorine, chlorine, bromine or a radical —NH—$R^5$, —NR$^6$R$^7$ or —S(O)$_n$—R$^{14}$ or $R^2$ and $R^3$ together represent one of the radicals

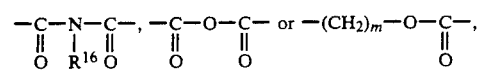

bridged via the positions 6 and 5, or $R^3$ and $R^4$ together represent an alkyl chain having 3 or 4 carbon atoms, which is bonded via the positions 4 and 3, $R^5$ represents hydrogen, straight-chain or branched alkyl having 1 to 6 carbon atoms or aryl having 6 to 10 carbon atoms, which is unsubstituted or monosubstituted to pentasubstituted by identical or different substituents, suitable aryl substituents being the aryl substituents listed under $R^3$, $R^6$ represents straight-chain or branched alkyl having 1 to 6 carbon atoms or aryl having 6 to 10 carbon atoms, which is unsubstituted or monosubstituted to pentasubstituted by identical or different substituents, suitable aryl substituents being the aryl substituents listed under $R^3$, $R^7$ represents straight-chain or branched alkyl having 1 to 6 carbon atoms or aryl having 6 to 10 carbon atoms, which is unsubstituted or monosubstituted to pentasubstituted by identical or different substituents, suitable aryl substituents being the aryl substituents listed under $R^3$, $R^8$ represents hydrogen, straight-chain or branched alkyl having 1 to 6 carbon atoms, aryl or aralkyl in each case having 6 to 10 carbon atoms in the aryl moiety and optionally 1 to 4 carbon atoms in the alkyl moiety and in each case unsubstituted or monosubstituted to pentasubstituted in the aryl moiety by identical or different substituents, suitable aryl substituents being the aryl substituents listed under $R^3$, $R^9$ represents alkyl or alkoxy having 1 to 6 carbon atoms, which is in each case straight-chain or branched, $R^{10}$ represents hydroxyl, straight-chain or branched hydroxyalkyloxy having 1 to 8 carbon atoms, straight-chain or branched halogenoalkyloxy having 1 to 8 carbon atoms and 1 to 17 identical or different halogen atoms, cycloalkyloxy having 3 to 6 carbon atoms which is unsubstituted or monosubstituted to polysubstituted by identical or different halogen substituents, alkoxy or alkylthio having 1 to 6 carbon atoms, which is in each case straight-chain or branched, straight-chain or branched alkoxyalkyloxy in each case having 1 to 6 carbon atoms in the alkoxy and alkyl moiety, aryloxy, arylthio, aralkyl or aralkyloxy in each case having 6 to 10 carbon atoms in the aryl moiety and optionally 1 to 8 carbon atoms in the alkyl moiety, and which is in each case unsubstituted or monosubstituted to pentasubstituted in the aryl moiety by identical or different substituents, suitable aryl substituents being the aryl substituents listed under $R^3$, or a group —OM, —$NHR^5$, —$NR^6R^7$ or —O—Z—$NR^5R^6$, $R^{11}$ represents hydrogen or straight-chain or branched alkyl having 1 to 6 carbon atoms, $R^{12}$ represents hydrogen or straight-chain or branched alkyl having 1 to 6 carbon atoms, $R^{13}$ represents straight-chain or branched alkyl having 1 to 6 carbon atoms, $R^{14}$ represents alkyl or alkoxy having 1 to 6 carbon atoms, which is in each case straight-chain or branched, aryl having 6 to 10 carbon atoms and unsubstituted or monosubstituted to pentasubstituted by identical or different substituents, suitable aryl substituents being the aryl substituents listed under $R^3$, or the group —OM, $R^{15}$ represents formyl, cyano or the group

$R^{16}$ represents hydrogen, straight-chain or branched alkyl having 1 to 6 carbon atoms or aryl having 6 to 10 carbon atoms, which is unsubstituted or monosubstituted to pentasubstituted by identical or different substituents, suitable aryl substituents being the aryl substituents listed under $R^3$, m represents a number 1 or 2 and M represents hydrogen or an equivalent of an appropriate alkali metal, alkaline earth metal or ammonium cation, n represents a number 0, 1 or 2, X and $X^1$ are identical or different and represent oxygen or sulphur, A represents hydrogen or an amino protecting group and Z represents a straight-chain or branched alkyl chain having 1 to 8 carbon atoms.

Preferred compounds to be used according to the invention are also addition products of acids and those substituted 2-cyclohexen-1-yl-amine derivatives of the formula (I) in which $R^1$, $R^2$, $R^3$ and $R^4$ have those meanings which have already been mentioned as preferable for these substituents in connection with the description of the substances to be used according to the invention.

The acids which can be adducted preferably include hydrohalic acids, such as, for example, hydrochloric acid and hydrobromic acid, in particular hydrochloric acid, in addition phosphoric acid, nitric acid, mono- and bifunctional carboxylic acids and hydroxycarboxylic acids, such as, for example, acetic acid, trifluoroacetic acid, maleic acid, succinic acid, fumaric acid, tartaric acid, citric acid, salicylic acid, sorbic acid and lactic acid, oleic acid, stearic acid, benzoic acid which is optionally monosubstituted to polysubstituted by nitro or halogen, gluconic acid, ascorbic acid, malic acid, sulphamic acid, sulphonic acids, such as, for example, p-toluenesulphonic acid, 1,5-naphthalenedisulphonic acid and methanesulphonic acid, and also imides, such as, for example, phthalimide, saccharin and thiosaccharin.

Additionally preferred compounds to be used according to the invention are also addition products of salts of metals of main groups I, II and III and of tin, and in addition salts of metals of sub-groups I, II, VII and VIII of the periodic table of the elements and those substituted 2-cyclohexen-1-yl-amine derivatives of the formula (I) in which $R^1$, $R^2$, $R^3$ and $R^4$ have the meanings which have already been mentioned as preferable for these substituents in connection with the description of the substances of the formula (I) to be used according to the invention.

In this connection, salts of copper, zinc, manganese, magnesium, calcium, tin, iron, cobalt and of nickel are particularly preferred. Possible anions of these salts are those which are derived from those acids which lead to physiologically tolerable addition products. In this connection, particularly preferred acids of this type are the hydrohalic acids, such as, for example, hydrochloric acid and hydrobromic acid, in addition phosphoric acid, nitric acid and sulphuric acid.

Particularly preferably used compounds of the formula (I) are those in which $R^1$ represents hydrogen, straight-chain or branched alkyl having 1 to 4 carbon atoms, or fluorine, chlorine or bromine, $R^2$ represents formyl, straight-chain or branched hydroxyalkyl having 1 to 4 carbon atoms in the alkyl moiety, cyano, nitro or one of the radicals

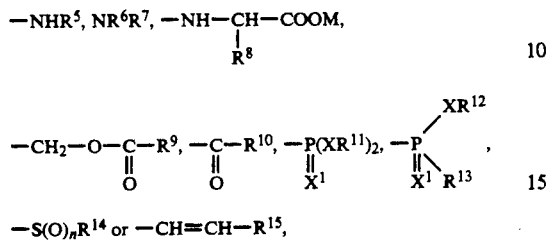

$-S(O)_nR^{14}$ or $-CH=CH-R^{15}$, $R^3$ and $R^4$ are identical or different and in each case represent hydrogen, alkyl or alkoxy having 1 to 6 carbon atoms, which is in each case straight-chain or branched, alkenyl, alkinyl, alkenyloxy or alkinyloxy in each case having 2 to 6 carbon atoms, which is in each case straight-chain or branched, alkoxyalkyloxy in each case having 1 to 6 carbon atoms in the individual alkyl moieties, phenyl or phenylalkyl optionally having 1 or 2 carbon atoms in the alkyl moiety and in each case unsubstituted in the phenyl moiety or monosubstituted to pentasubstituted by identical or different substituents, suitable phenyl substituents being: fluorine, chlorine, bromine, nitro, cyano, amino, $C_1$-$C_2$-alkyl, $C_1$-$C_3$-alkoxy or $C_1$-$C_2$-alkylthio, halogeno-($C_1$-$C_2$)-alkyl, halogeno-($C_1$-$C_2$)-alkoxy and halogeno-($C_1$-$C_2$)-alkylthio in each case having 1 to 5 identical or different fluorine and/or chlorine atoms, furthermore a heterocyclic 5- or 6-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which is unsubstituted or monosubstituted to trisubstituted by identical or different substituents and optionally bonded via a methylene group, suitable substituents for the heterocycle in each case being: fluorine, chlorine, bromine, nitro, cyano, amino, $C_1$-$C_2$-alkyl, $C_1$-$C_2$-alkoxy or $C_1$-$C_2$-alkylthio, halogeno-($C_1$-$C_2$)-alkyl, halogeno-($C_1$-$C_2$)-alkoxy or halogeno-($C_1$-$C_2$)-alkylthio in each case having 1 to 5 identical or different fluorine and/or chlorine atoms, and di-($C_1$-$C_2$)-alkylamino, furthermore fluorine, chlorine, bromine or one of the radicals $-NH-R^5$, $-NR^6R^7$ or $-S(O)_n-R^{14}$ or $R^2$ and $R^3$ together represent one of the radicals

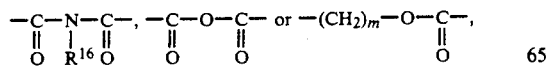

bridged via the positions 6 and 5, or $R^3$ and $R^4$ together represent an alkyl chain having 3 or 4 carbon atoms, which is bonded via the positions 4 and 3, $R^5$ represents hydrogen, straight-chain or branched alkyl having 1 to 4 carbon atoms or phenyl which is unsubstituted or monosubstituted to pentasubstituted by identical or different substituents, suitable phenyl substituents being the phenyl substituents listed under $R^3$, $R^6$ represents straight-chain or branched alkyl having 1 to 4 carbon atoms or phenyl which is unsubstituted or monosubstituted to pentasubstituted by identical or different substituents, suitable phenyl substituents being the phenyl substituents listed under $R^3$, $R^7$ represents straight-chain or branched alkyl having 1 to 4 carbon atoms or phenyl which is unsubstituted or monosubstituted to pentasubstituted by identical or different substituents, suitable phenyl substituents being the phenyl substituents listed under $R^3$, $R^8$ represents hydrogen, straight-chain or branched alkyl having 1 to 4 carbon atoms, phenyl or phenylalkyl optionally having 1 or 2 carbon atoms in the alkyl moiety and in each case unsubstituted or monosubstituted to pentasubstituted in the phenyl moiety by identical or different substituents, suitable phenyl substituents being the phenyl substituents listed under $R^3$, $R^9$ represents alkyl or alkoxy having 1 to 4 carbon atoms, which is in each case straight-chain or branched, $R^{10}$ represents hydroxyl, straight-chain or branched hydroxyalkyloxy having 1 to 6 carbon atoms, straight-chain or branched halogenoalkyloxy having 1 to 6 carbon atoms and 1 to 13 identical or different halogen atoms, cycloalkyloxy having 3 to 6 carbon atoms and unsubstituted or monosubstituted to trisubstituted by identical or different substituents from the series comprising fluorine, chlorine and bromine, alkoxy or alkylthio having 1 to 4 carbon atoms, which is in each case straight-chain or branched, straight-chain or branched alkoxyalkyloxy in each case having 1 to 4 carbon atoms in the alkoxy or alkyl moiety, phenyloxy, phenylthio, phenylalkyl or phenylalkyloxy in each case optionally having 1 to 6 carbon atoms in the alkyl moiety and in each case unsubstituted or monosubstituted to pentasubstituted in the phenyl moiety by identical or different substituents, suitable phenyl substituents being the phenyl substituents listed under $R^3$ or a group $-OM$, $-NHR^5$, $-NR^6R^7$ or $-O-Z-NR^5R^6$, $R^{11}$ represents hydrogen or straight-chain or branched alkyl having 1 to 4 carbon atoms, $R^{12}$ represents hydrogen or straight-chain or branched alkyl having 1 to 4 carbon atoms, $R^{13}$ represents straight-chain or branched alkyl having 1 to 4 carbon atoms, $R^{14}$ represents alkyl or alkoxy having 1 to 4 carbon atoms, which is in each case straight-chain or branched, phenyl which is unsubstituted or monosubstituted to pentasubstituted by identical or different substituents, suitable phenyl substituents being the phenyl substituents listed under $R^3$, or the group $-OM$, $R^{15}$ represents formyl, cyano or the group

R$^{16}$ represents hydrogen, straight-chain or branched alkyl having 1 to 4 carbon atoms or phenyl which is unsubstituted or monosubstituted to pentasubstituted by identical or different substituents, suitable phenyl substituents being the phenyl substituents listed under R$^3$, m represents a number 1 or 2 and M represents hydrogen or an equivalent of an appropriate sodium, potassium or ammonium cation, n represents a number 0, 1 or 2, X and X$^1$ are identical or different and represent oxygen or sulphur, A represents hydrogen or an amino protecting group and Z represents a straight-chain or branched alkyl chain having 1 to 6 carbon atoms.

The expression "amino protecting group" is generally known and relates to groups which are suitable for protecting (for blocking) an amino group from chemical reactions, but which are easily removable after the desired reaction has been carried out in other positions in the molecule. Typical of such groups are in particular unsubstituted or substituted acyl, aryl, for example DNP (2,4-dinitrophenyl), aralkoxymethyl, for example BOM (N-(benzyloxy)methyl) or aralkyl groups (for example benzyl, 4-nitrobenzyl, triphenylmethyl). As the amino protecting groups are removed after the desired reaction (or reaction sequence), their nature and size is otherwise not critical; however, those having 1-20, in particular 1-8 carbon atoms, are preferred. The expression "acyl group" is to be understood in the widest sense in connection with the present invention. It includes acyl groups derived from aliphatic, araliphatic, aromatic or heterocyclic carboxylic acids or sulphonic acids and in particular alkoxycarbonyl, aryloxycarbonyl and above all aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA (phenoxyacetyl); alkoxycarbonyl such as methoxycarbonyl, ethoxycarbonyl, 2,2,2-trichloroethoxycarbonyl, BOC (tert.-butoxycarbonyl),2-iodoethoxycarbonyl;aralkyloxycarbonyl such as CBZ ("carbobenzoxy") and 4-methoxybenzyloxycarbonyl. Preferred amino protecting groups are benzyl, acetyl, methoxycarbonyl, allyloxycarbonyl, trichloroethyloxycarbonyl, (±)-menthyloxycarbonyl, tert-butoxycarbonyl and benzyloxycarbonyl.

The application further relates to the use of substituted 2-cyclohexen-1-yl-amine derivatives of the formula (Ia)

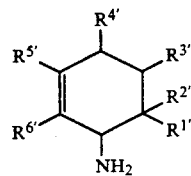

in which

R$^{1'}$ represents hydrogen, alkyl or halogen,

R$^{2'}$ represents formyl, hydroxyalkyl, cyano, nitro or one of the radicals

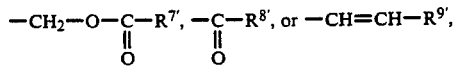

R$^{3'}$, R$^{4'}$, R$^{5'}$ and R$^{6'}$ are identical or different and in each case represent hydrogen, alkyl, alkenyl, alkinyl, alkoxy, alkenyloxy, alkinyloxy, unsubstituted or substituted aryl, unsubstituted or substituted aralkyl, unsubstituted or substituted heteroaryl, unsubstituted or substituted heterocyclylalkyl, alkoxyalkyloxy or halogen, where at least two of the radicals R$^{3'}$, R$^{4'}$, R$^{5'}$ or R$^{6'}$ represent hydrogen, R$^{7'}$ represents alkyl or alkoxy, R$^{8'}$ represents hydroxyl, hydroxyalkyloxy, halogenoalkyloxy, alkoxy, alkoxyalkyloxy, unsubstituted or substituted cycloalkyloxy, unsubstituted or substituted aralkyloxy, unsubstituted or substituted aryloxy, unsubstituted or substituted aralkyl, alkylthio, unsubstituted or substituted arylthio or a group —O—Z—NR$^{11'}$R$^{12'}$, —NHR$^{10'}$, —NR$^{11'}$R$^{12'}$ or —OM, R$^{9'}$ represents formyl, cyano or the group

R$^{10'}$ represents hydrogen, alkyl or unsubstituted or substituted aryl,

R$^{11'}$ and R$^{12'}$ are identical or different and in each case represent alkyl or unsubstituted or substituted aryl, Z represents a straight-chain or branched alkyl chain and M represents hydrogen or an equivalent of an appropriate alkali metal, alkaline earth metal or ammonium cation, or R$^{2'}$ and R$^{3'}$ together represent one of the radicals

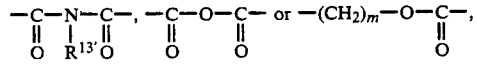

bridged via the positions 6 and 5, in which

R$^{13'}$ represents hydrogen, alkyl or unsubstituted or substituted aryl and m represents a number 1 or 2, or R$^{4'}$ and R$^{5'}$ together represent an alkyl chain having 3 or 4 carbon atoms, which is bonded via the positions 4 and 3, and their acid addition salts and metal salt complexes.

Preferred compounds of the formula (Ia) are those in which

R$^{1'}$ represents hydrogen, straight-chain or branched alkyl having 1 to 6 carbon atoms or fluorine, chlorine or bromine, R$^{2'}$ represents formyl, straight-chain or branched hydroxyalkyl having 1 to 8 carbon atoms in the alkyl moiety, cyano, nitro or one of the radicals

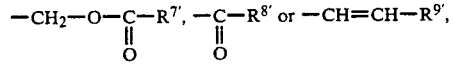

$R^{3\prime}$, $R^{4\prime}$, $R^{5\prime}$ and $R^{6\prime}$ are identical or different and in each case represent hydrogen, alkyl or alkoxy having 1 to 8 carbon atoms, which is in each case straight-chain or branched, alkenyl, alkinyl, alkenyloxy or alkinyloxy in each case having 2 to 8 carbon atoms, which is in each case straight-chain or branched, alkoxyalkyloxy in each case having 1 to 8 carbon atoms in the individual alkyl moieties, aryl or aralkyl in each case having 6 to 10 carbon atoms in the aryl moiety and optionally 1 to 4 carbon atoms in the alkyl moiety and in each case unsubstituted or monosubstituted to pentasubstituted in the aryl moiety by identical or different substituents, suitable aryl substituents being: halogen, nitro, cyano, amino, $C_1$-$C_4$-alkyl, $C_1$-$C_4$-alkoxy or $C_1$-$C_4$-alkylthio, halogeno-($C_1$-$C_4$)-alkyl, halogeno-($C_1$-$C_4$)-alkoxy or halogeno-($C_1$-$C_4$)-alkylthio in each case having 1 to 9 identical or different halogen atoms, and di-($C_1$-$C_4$)-alkylamino, furthermore a heterocyclic 5- or 6-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl which is unsubstituted or monosubstituted to trisubstituted by identical or different substituents and optionally bonded via a methylene group, suitable substituents for the heterocycle in each case being: halogen, nitro, cyano, amino, $C_1$-$C_4$-alkyl, $C_1$-$C_4$-alkoxy or $C_1$-$C_4$-alkylthio, halogeno-($C_1$-$C_4$)-alkyl, halogen-($C_1$-$C_4$)-alkoxy or halogeno-($C_1$-$C_4$)-alkylthio in each case having 1 to 9 identical or different halogen atoms and di-($C_1$-$C_4$)-alkylamino, furthermore fluorine, chlorine or bromine, where at least two of the radicals $R^{3\prime}$, $R^{4\prime}$, $R^{5\prime}$ or $R^{6\prime}$ represent hydrogen, $R^{7\prime}$ represents alkyl or alkoxy having 1 to 6 carbon atoms, which is in each case straight-chain or branched, $R^{8\prime}$ represents hydroxyl, straight-chain or branched hydroxyalkyloxy having 1 to 8 carbon atoms, straight-chain or branched halogenoalkyloxy having 1 to 8 carbon atoms and 1 to 17 identical or different halogen atoms, cycloalkyloxy having 3 to 6 carbon atoms and unsubstituted or monosubstituted to polysubstituted by identical or different halogen substituents, alkoxy or alkylthio having 1 to 6 carbon atoms, which is in each case straight-chain or branched, straight-chain or branched alkoxyalkyloxy in each case having 1 to 6 carbon atoms in the alkoxy or alkyl moiety, aryloxy, arylthio, aralkyl or aralkyloxy in each case having 6 to 10 carbon atoms in the aryl moiety and optionally 1 to 8 carbon atoms in the alkyl moiety and in each case unsubstituted or monosubstituted to pentasubstituted in the aryl moiety by identical or different substituents, suitable aryl substituents being the abovementioned aryl substituents, or a group —O—Z—NR$^{11\prime}$R$^{12\prime}$, —NHR$^{10\prime}$, —NR$^{11\prime}$R$^{12\prime}$ or —OM, $R^{9\prime}$ represents formyl, cyano or the group

$R^{10\prime}$ represents hydrogen, straight-chain or branched alkyl having 1 to 6 carbon atoms or aryl having 6 to 10 carbon atoms, which is unsubstituted or monosubstituted to pentasubstituted by identical or different substituents, suitable aryl substituents being the abovementioned aryl substituents, $R^{11\prime}$ represents straight-chain or branched alkyl having 1 to 6 carbon atoms or aryl having 6 to 10 carbon atoms, which is unsubstituted or monosubstituted to pentasubstituted by identical or different substituents, suitable aryl substituents being the abovementioned aryl substituents, $R^{12\prime}$ represents straight-chain or branched alkyl having 1 to 6 carbon atoms or aryl having 6 to 10 carbon atoms, which is unsubstituted or monosubstituted to pentasubstituted by identical or different substituents, suitable aryl substituents being the abovementioned aryl substituents, M represents hydrogen or an equivalent of an appropriate alkali metal, alkaline earth metal or ammonium cation and Z represents a straight-chain or branched alkyl chain having 1 to 8 carbon atoms, or $R^{2\prime}$ and $R^{3\prime}$ together represent one of the radicals

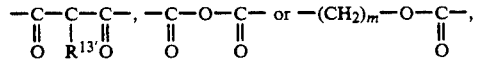

bridged via the positions 6 and 5, in which $R^{13\prime}$ represents hydrogen, straight-chain or branched alkyl having 1 to 6 carbon atoms or aryl having 6 to 10 carbon atoms, which is unsubstituted or monosubstituted to pentasubstituted by identical or different substituents, suitable aryl substituents being the abovementioned aryl substituents and m represents a number 1 or 2, or $R^{4\prime}$ and $R^{5\prime}$ together represent an alkyl chain having 3 or 4 carbon atoms, which is bonded via the positions 4 and 3.

Preferred compounds according to the invention are also addition products of acids and those substituted 2-cyclohexen-1-yl-amine derivatives of the formula (Ia) in which $R^{1\prime}$, $R^{2\prime}$, $R^{3\prime}$, $R^{4\prime}$, $R^{5\prime}$ and $R^{6\prime}$ have the abovementioned meanings.

The acids which can be adducted preferably include hydrohalic acids, such as, for example, hydrochloric acid and hydrobromic acid, in particular hydrochloric acid, in addition phosphoric acid, nitric acid, mono- and bifunctional carboxylic acids and hydroxycarboxylic acids, such as, for example, acetic acid, trifluoroacetic acid, maleic acid, succinic acid, fumaric acid, tartaric acid, citric acid, salicylic acid, sorbic acid and lactic acid, oleic acid, stearic acid, benzoic acid which is optionally monosubstituted or polysubstituted by nitro or halogen, gluconic acid, ascorbic acid, malic acid, sulphamic acid, sulphonic acids, such as, for example, p-toluenesulphonic acid, 1,5-naphthalenedisulphonic acid and methanesulphonic acid, and also imides, such as, for example, phthalimide, saccharin and thiosaccharin.

Additionally preferred compounds according to the invention are also addition products of salts of metals of main groups I, II and III and of tin, and in addition salts of metals of sub-groups I, II, VII and VIII of the periodic table of the elements and those substituted 2-cyclohexen-1-yl-amine derivatives of the formula (Ia) in which $R^{1'}$, $R^{2'}$, $R^{3'}$, $R^{4'}$, $R^{5'}$ and $R^{6'}$ have the abovementioned meanings.

In this connection, salts of copper, zinc, manganese, magnesium, calcium, tin, iron, cobalt and of nickel are particularly preferred. Possible anions of these salts are those which are derived from those acids which lead to physiologically tolerable addition products. In this connection, particularly preferred acids of this type are the hydrohalic acids, such as, for example, hydrochloric acid and hydrobromic acid, in addition phosphoric acid, nitric acid and sulphuric acid.

Particularly preferred compounds of the formula (Ia) are those in which $R^{1'}$ represents hydrogen, straight-chain or branched alkyl having 1 to 4 carbon atoms, or fluorine, chlorine or bromine, $R^{2'}$ represents formyl, straight-chain or branched hydroxyalkyl having 1 to 4 carbon atoms in the alkyl moiety, cyano, nitro or one of the radicals

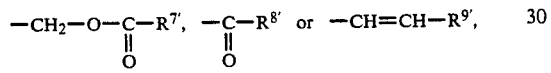

$R^{3'}$, $R^{4'}$, $R^{5'}$ and $R^{6'}$ are identical or different and in each case represent hydrogen, alkyl or alkoxy having 1 to 6 carbon atoms, which is in each case straight-chain or branched, alkenyl, alkinyl, alkenyloxy or alkinyloxy in each case having 2 to 6 carbon atoms, which is in each case straight-chain or branched, alkoxyalkyloxy in each case having 1 to 6 carbon atoms in the individual alkyl moieties, phenyl or phenylalkyl optionally having 1 or 2 carbon atoms in the alkyl moiety and in each case unsubstituted or monosubstituted to trisubstituted in the phenyl moiety by identical or different substituents, suitable phenyl substituents being: fluorine, chlorine, bromine, nitro, cyano, amino, $C_1$–$C_2$-alkyl, $C_1$–$C_3$-alkoxy, $C_1$–$C_2$-alkylthio, halogeno-($C_1$–$C_2$)-alkyl, halogeno-($C_1$–$C_2$)-alkoxy, halogeno-($C_1$–$C_2$)-alkylthio in each case having 1 to 5 identical or different fluorine and/or chlorine atoms and di-($C_1$–$C_2$)-alkylamino, furthermore a heterocyclic five- or six-membered group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which is unsubstituted or monosubstituted to trisubstituted by identical or different substituents and optionally bonded via a methylene group, suitable substituents for the heterocycle in each case being: fluorine, chlorine, bromine, nitro, cyano, amino, $C_1$–$C_2$-alkyl, $C_1$–$C_2$-alkoxy or $C_1$–$C_2$-alkylthio, halogeno-($C_1$–$C_2$)-alkyl, halogeno-($C_1$–$C_2$)-alkoxy or halogeno-($C_1$–$C_2$)-alkylthio in each case having 1 to 5 identical or different fluorine and/or chlorine atoms, and di-($C_1$–$C_2$)-alkylamino, furthermore fluorine, chlorine or bromine, where at least two of the radicals $R^{3'}$, $R^{4'}$, $R^{5'}$ and $R^{6'}$ represent hydrogen, $R^{7'}$ represents alkyl or alkoxy having 1 to 4 carbon atoms, which is in each case straight-chain or branched, $R^{8'}$ represents hydroxyl, straight-chain or branched hydroxyalkyloxy having 1 to 6 carbon atoms, straight-chain or branched halogenoalkyloxy having 1 to 6 carbon atoms and 1 to 13 identical or different halogen atoms, cycloalkyloxy having 3 to 6 carbon atoms, which is unsubstituted or monosubstituted to trisubstituted by identical or different fluorine, chlorine, or bromine substituents, alkoxy or alkylthio having 1 to 4 carbon atoms, which is in each case straight-chain or branched, straight-chain or branched alkoxyalkyloxy in each case having 1 to 4 carbon atoms in the alkoxy or alkyl moiety, phenyloxy, phenylthio, phenylalkyl or phenylalkyloxy in each case optionally having 1 to 6 carbon atoms in the alkyl moiety and in each case unsubstituted or monosubstituted to trisubstituted in the phenyl moiety by identical or different substituents, suitable phenyl substituents being the abovementioned phenyl substituents, or a group —O—Z—$NR^{11'}R^{12'}$, —$NHR^{10'}$, —$NR^{1'}R^{12'}$ or —OM, $R^{9'}$ represents formyl, cyano or the group

$R^{10'}$ represents hydrogen, straight-chain or branched alkyl having 1 to 4 carbon atoms or phenyl which is unsubstituted or monosubstituted to trisubstituted by identical or different substituents, suitable phenyl substituents being the abovementioned phenyl substituents, $R^{11'}$ represents straight-chain or branched alkyl having 1 to 4 carbon atoms or phenyl which is unsubstituted or monosubstituted to trisubstituted by identical or different substituents, suitable phenyl substituents being the abovementioned phenyl substituents, $R^{12'}$ represents straight-chain or branched alkyl having 1 to 4 carbon atoms or phenyl which is unsubstituted or monosubstituted to trisubstituted by identical or different substituents, suitable phenyl substituents being the abovementioned phenyl substituents, M represents hydrogen or an equivalent of an appropriate alkali metal, alkaline earth metal or ammonium cation and Z represents a straight-chain or branched alkyl chain having 1 to 6 carbon atoms, or $R^{2'}$ and $R^{3'}$ together represent one of the radicals

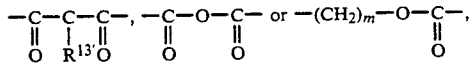

bridged via the positions 6 and 5, $R^{13'}$ represents hydrogen, straight-chain or branched alkyl having 1 to 6 carbon atoms or phenyl which is unsubstituted or monosubstituted to trisubstituted by identical or different substituents, suitable phenyl substituents being the abovementioned phenyl substituent and m represents a number 1 or 2, or R$^{4'}$ and R$^{5'}$ together represent an alkyl chain having 3 or 4 carbon atoms, which is bonded via the positions 4 and 3.

In this connection, the same acid addition salts and metal salt complexes are to be mentioned which have already been mentioned in the description of the preferred substituted 2-cyclohexen-1-yl-amine derivatives of the formula (Ia) according to the invention.

The substituted 2-cyclohexen-1-yl-amine derivatives of the formula (Ia) are obtained when A) 2-cyclohexen-1-yl-carboxylic acid derivatives of the formula (II)

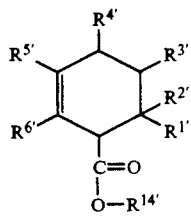

(II)

in which

R$^{1'}$, R$^{2'}$, R$^{3'}$, R$^{4'}$, R$^{5'}$ and R$^{6'}$ have the abovementioned meaning and R$^{14'}$ represents hydrogen, methyl or ethyl, are treated with esters of chloroformic acid in a generally customary manner, according to Curtius, if appropriate in the presence of a diluent, such as, for example, acetone and in the presence of a base, such as, for example, N,N-diisopropylamine, at temperatures between $-15°$ C. and $+10°$ C., and an azide, such as, for example, sodium azide, is added to this reaction mixture, if appropriate in the presence of a diluent, such as, for example, water, at temperatures between $-5°$ C. and $+25°$ C., and the intermediately formed isocyanate of the formula (IIa)

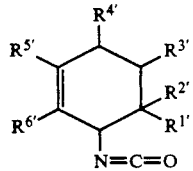

(IIa)

in which

R$^{1'}$, R$^{2'}$, R$^{3'}$, R$^{4'}$, R$^{5'}$ and R$^{6'}$ have the abovementioned meaning, is hydrolysed with water, if appropriate in the presence of an acid or of a base, and the amines thus obtained are optionally converted into acid addition salts and metal salt complexes [cf. *J. Org. Chem.* 26, (1961), 3511].

The substituted 2-cyclohexen-1-yl-amine derivatives of the formula (Ia) ar additionally obtained B) from the 2-cyclohexene derivatives of the formula (IIb)

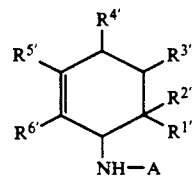

(IIb)

in which

R$^{1'}$, R$^{2'}$, R$^{3'}$, R$^{4'}$, R$^{5'}$ and R$^{6'}$ have the abovementioned meaning and A represents an amino protecting group, in a manner known per se by customary methods, for example by solvolysis, such as hydrolysis, acidolysis, by reduction, such as, for example, by hydrogenolysis in the presence of a hydrogenation catalyst or by means of a reduction system formed from a metal and proton-eliminating agent, it being possible, depending on the nature of the protecting group, to use various (even different) and also selective elimination methods, if appropriate in the presence of a suitable solvent or diluent or of a mixture thereof, working, as required, with cooling, at room temperature or with warming, for example in a temperature range from about $-10°$ C. up to the boiling temperature of the reaction medium, preferably from about $-10°$ C. to about 150° C., and, if necessary, in a closed vessel, under pressure, in an inert gas atmosphere and/or under anhydrous conditions and optionally converting the products thus obtained into acid addition salts or metal salt complexes (cf. Protective .Groups in Organic Synthesis, Th. W. Greene, Wiley Interscience, 1981).

The formyl, acetyl or 2,2,2-trichloroacetyl group mentioned as an amino protecting group at the beginning, inter alia, can be eliminated, for example, by hydrolysis.

The hydrolysis is carried out in a manner known per se with the aid of water, being advantageously carried out in the presence of an acid or base assisting hydrolysis, if appropriate in the presence of an inert solvent or diluent and/or with cooling or warming.

Possible acids are, for example, inorganic acids, such as mineral acids, for example sulphuric acid, phosphoric acid or hydrohalic acids, organic carboxylic acids, such as lower alkanecarboxylic acids, for example glacial acetic acid, such as optionally unsaturated dicarboxylic acids, for example oxalic, malonic, maleic or fumaric acid, or such as hydroxycarboxylic acids, for example tartaric acid or citric acid or sulphonic acids, such as C$_1$–C$_7$-alkane- or optionally substituted benzenesulphonic acid, for example methane- or p-toluenesulphonic acid.

Suitable bases are, for example, alkali metal hydroxides, hydrides, amides, alkoxides, carbonates, triphenylmethylides, di-C$_1$–C$_7$-alkylamides, amino-C$_1$–C$_7$-alkylamides or C$_1$–C$_7$-alkylsilylamides, naphthalene-amines, C$_1$–C$_7$-alkylamines, basic heterocycles, ammonium hydroxides and carbocyclic amines. By way of example, lithium hydroxide, sodium hydroxide, hydride, amide and ethoxide, potassium tertbutoxide and carbonate, lithium triphenylmethylide and diisopropylamide, potassium 3-(aminopropyl)amide and bis-(trimethylsilyl)-amide, dimethylaminonaphthalene, di- or triethylamine, pyridine, benzyltrimethyl-ammonium hydroxide, 1,5-diazabicyclo[4.3.0]non-5-ene (DBN) and 1,8-diaza-bicyclo[5.4.0]undec-7-ene (DBU) may be mentioned.

Acidolysis is carried out, for example, using strong acids, expediently with trifluoroacetic acid or perchloric acid, but also with other strong inorganic acids such as hydrochloric acid or sulphuric acid, strong organic carboxylic acids such as trichloroacetic acid or sulphonic acids such as benzene- or p-toluenesulphonic acid. The presence of an additional inert solvent is possible. Suitable inert solvents are preferably organic, for example carboxylic acids such as acetic acid, ethers such as tetrahydrofuran or dioxane, amides such as dimethylformamide (DMF), halogenated hydrocarbons such as dichloromethane, and in addition also alcohols such as methanol, ethanol or isopropanol and also water.

In addition, mixtures of the abovementioned solvents are also suitable. Trifluoroacetic acid is preferably used in excess without addition of another solvent, perchloric acid is preferably used in the form of a mixture of acetic acid and 70% strength perchloric acid in the ratio 9:1. The reaction temperatures for these solvolyses are expediently between about 0° and about 50° C.; the reaction is preferably carried out between 15° and 30° C. (room temperature).

The BOC group can preferably be eliminated, for example, using 40% strength trifluoroacetic acid in methylene chloride or using about 3 to 5 N hydrochloric acid in dioxane at 15°–30° C., the FMOC group (9-fluorenylmethyloxycarbonyl) using an about 5 to 20% strength solution of dimethylamine, diethylamine or piperidine in dimethylformamide at 15°–30° C. Elimination of the DNP group (2,4-dinitrophenyl) is also carried out, for example, using an about 3 to 10% strength solution of 2-mercaptoethanol in dimethylformamide/water at 15°–30° C. Protecting groups which can be removed by hydrogenolysis (for example BOM, CBZ or benzyl) can be eliminated, for example, by treating with hydrogen in the presence of a catalyst (for example a noble metal catalyst such as palladium, expediently on a support such as carbon). Suitable solvents in this case are the abovementioned, in particular, for example, alcohols such as methanol or ethanol or amides such as dimethylformamide. The hydrogenolysis is as a rule carried out at temperatures from about 0° to 100° C. and at a pressure of about 1 to 200 bar, preferably at 20° to 30° C. and at 1 to 10 bar. Hydrogenolysis of the CBZ group is easily carried out, for example, on 5 to 10% strength Pd-carbon in methanol at 20°–30° C.

Amino protecting groups which may be mentioned, which are eliminated by means of a reduction system formed from a metal and proton-eliminating agent, are, for example, (4-nitro)-benzyloxycarbonyl, 2-iodo- or 2,2,2-trichloroethoxycarbonyl or phenacyloxycarbonyl.

The metal component of the metallic reduction system is, for example, a base metal, such as alkali metal or alkaline earth metal, for example lithium, sodium, potassium, magnesium or calcium, or transition metal, for example zinc, tin, iron or titanium, while suitable proton-eliminating agents are, for example, protonic acids of the abovementioned type, such as hydrochloric or acetic acid $C_1$–$C_7$-alcohols, such as ethanol, and/or amines or ammonia. Such systems are, for example sodium/ammonia, zinc/hydrochloric or acetic acid, or zinc/ethanol.

4-Nitrobenzyloxycarbonyl can additionally be cleaved, for example, using a dithionite, such as sodium dithionite, phenacylocarbonyl and 2-halogeno-$C_2$–$C_7$-alkanoyl, for example with the aid of a nucleophilic reagent, such as a thiolate, for example sodium thiophenoxide, or thiourea and base and subsequent hydrolysis, and allyl or but-2-enyl, with the aid of a rhodium-(III) halide, such as rhodium(III) chloride.

The known compounds of the formula (I) can be prepared in analogy to the new compounds of the formula (Ia).

If, for example, methyl 2-carboxy-5-methyl-cyclohex-3-ene-carboxylate and ethyl chloroformate are used as starting substances and N,N-diisopropylethyamine is used as a base for the first step and sodium azide and water are used for the second step, the course of the reaction of preparation process (A) can be represented by the following equation:

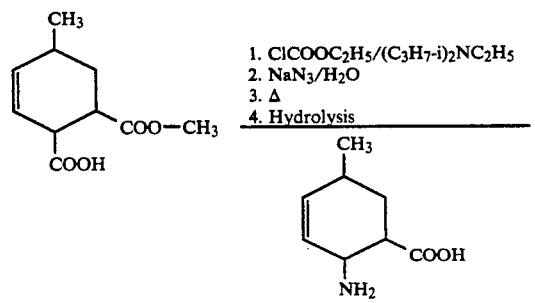

If, for example, tert-butyl (3-methyl-6-carboxy-2-cyclohexen-1-yl)-carbamate and 1N hydrochloric acid are used as starting substances, the course of the reaction of preparation process (B) can be represented by the following equation:

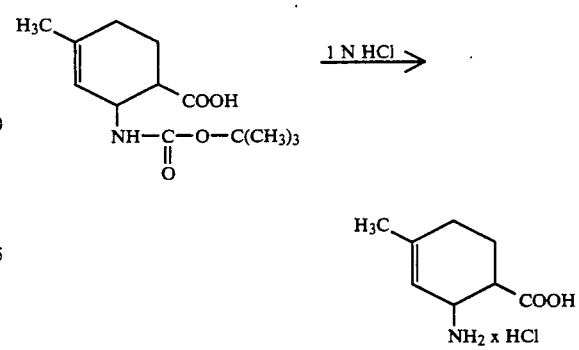

Formula (II) provides a general definition of the 2-cyclohexen-1-yl-carboxylic acid derivatives required as starting substances for carrying out preparation process (A). In this formula (II), $R^{1'}$, $R^{2'}$, $R^{3'}$, $R^{4'}$, $R^{5'}$ and $R^{6'}$ preferably or in particular represent those substituents which have been mentioned above as preferred or as particularly preferred for these radicals in the description of the new 2-cyclohexen-1-yl-amine derivatives of the formula (Ia).

The 2-cyclohexen-1-yl-carboxylic acid derivatives of the formula (II) are known in some cases and/or can be prepared by known processes in a simple analogous manner (cf. Houben-Weyl, Methoden der Organischen Chemie (Methods of Organic Chemistry), 4th Edition, E. Müller, Ed. Vol. 5/1c, Georg Thieme Verlag, Stuttgart, 1970, 977; J. Chem. Soc. Perkin Trans. 1, 1557–62, 1981), for example by cyclising the known dienophiles of the formula (III)

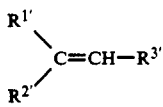

in which R$^{1'}$, R$^{2'}$ and R$^{3'}$ have the abovementioned meaning, with the appropriate dienecarboxylic acid derivatives of the formula (IV)

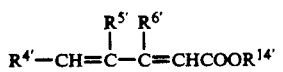

in which

R$^{4'}$, R$^{5'}$ and R$^{6'}$ have the abovementioned meaning and

R$^{14'}$ represents hydrogen, methyl or ethyl, if appropriate in the presence of a diluent, if appropriate in the presence of a catalyst, if appropriate in the presence of an inert gas and if appropriate under pressure, at temperatures between −50° C. and 150° C.

Formula (III) provides a general definition of the dienophiles required as starting substances for the preparation of the 2-cyclohexen-1-yl-carboxylic acid derivatives of the formula (II) and the 2-cyclohexene derivatives of the formula (IIb). In this formula (III), R$^{1'}$, R$^{2'}$ and R$^{3'}$ represent those radicals which have already been mentioned for these substituents in connection with the description of the compounds of the formula (Ia) according to the invention.

The following may be mentioned by way of example of, but not limiting, compounds of the formula (III): acrylic acid, esters of acrylic acid, such as, for example, methyl acrylate, ethyl acrylate, acrylamides, such as, for example, N,N-dimethylacrylamide, acrylonitrile, chloroacrylonitrile, maleic anhydride, maleimides, such as, for example, N-phenylmaleimide, vinyl derivatives, such as, for example, vinylphosphonic acid, dimethyl vinylphosphonate and ω-nitrostyrene.

The compounds of the formula (III) are generally known compounds of organic chemistry.

Formula (IV) provides a general definition of the dienecarboxylic acid derivatives additionally required as starting substances for the preparation of the 2-cyclohexen-1-yl-carboxylic acid derivatives of the formula (II). In this formula (IV), R$^{4'}$, R$^{5'}$ and R$^{6'}$ represent those radicals which have already been mentioned for these substituents in connection with the description of the compounds of the formula (Ia) according to the invention.

The dienecarboxylic acid derivatives of the formula (IV) are known and/or can be prepared by processes known from the literature in a simple, analogous manner (cf. 'Some Modern Methods of Organic Synthesis', W. Carruthers, Cambridge University Press, 1986, p. 125; Acc. Chem. Res., 1979, 146).

Formula (IIb) provides a general definition of the 2-cyclohexene derivatives required as starting substances for carrying out preparation process (B). In this formula (IIb), R$^{1'}$, R$^{2'}$, R$^{3'}$, R$^{4'}$, R$^{5'}$, R$^{6'}$ and A preferably or in particular represent those substituents which have already been mentioned above as preferred or as particularly preferred for these radicals in the description of the new 2-cyclohexen-1-yl-amine derivatives of the formula (Ia).

The 2-cyclohexene derivatives of the formula (IIb) are new in some cases and part of the present invention.

The known compounds and their enantiomers and isomers listed below are excluded: methyl 6-formyl-5-{[(phenylmethoxy)-carbonyl]-amino}-3-cyclohexene-1-carboxylate and methyl 6-(3-oxo-1-propenyl)-5-{[(phenylmethoxy)-carbonyl]-amino)}-3-cyclohexene-1-carboxylate (cf. J. Med. Chem., 29, 1–8, 1986; J. Med. Chem., 24, 788–94, 1981), methyl 3-cyclohexene-2-[(trichloroacetyl)amino]-1-carboxylate, 2,2,2-trichloro-N-(6-formyl-2-cyclohexen-1-yl)-acetamide, ethyl (6-formyl-5-methyl-2-cyclohexen-1-yl)-carbamate, methyl 2-[(ethoxy-carbonyl)amino]-6-methyl-3-cyclohexene-1-carboxylate, methyl 2-[(ethoxycarbonyl)-amino]-5-methyl-3-cyclohexene-1-carboxylate, methyl 2-[(ethoxycarbonyl)-amino]-3-cyclohexene-1-carboxylate, ethyl 3-(2-[(ethoxycarbonyl)amino]-6-methyl-3-cyclohexen-1-yl}-2-propenoate, phenylmethyl (6-formyl-5-propyl-2-cyclohexen-1-yl)-carbamate, phenylmethyl (6-formyl-5-methyl-2-cyclohexen-1-yl)carbamate, methyl 2-[(phenoxycarbonyl)-amino]-3-cyclohexene-1-carboxylate and ethyl 3-<6-methyl-2-{[(phenylmethoxy)-carbonyl]-amino}-3-cyclohexen-1-yl>-2-propenoate (cf. J. Am. Chem. Soc., 103, 2816–22, 1981; J. Am. Chem. Soc., 100, 3182–9, 1978; J.,Am. Chem. Soc., 100, 5179–85, 1978 and Tetrahedron Lett. 25, 2183–6, 1984), phenylmethyl (6-formyl-5-pentyl-2-cyclohexen-1-yl)-carbamate (cf. J. Org. Chem., 46, 2833–5, 1981) and phenylmethyl {6-formyl-5-[2-(methoxymethoxy)-ethyl]-2-cyclohexen-1-yl}-carbamate (cf. J. Am. Chem. Soc., 105, 5373–9, 1983).

The new 2-cyclohexene derivatives of the formula (IIb) are obtained by cyclising dienophiles of the formula (III)

in which

R$^{1'}$, R$^{2'}$ and R$^{3'}$ have the abovementioned meaning, (B/a) with N-acyl-1-amino-1,3-butadiene derivatives of the formula (IVa)

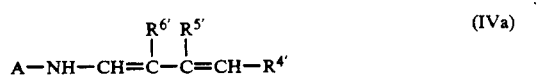

in which R$^{4'}$, R$^{5'}$, R$^{6'}$ and A have the abovementioned meaning, if appropriate in the presence of a diluent, if appropriate in the presence of a catalyst, if appropriate in the presence of an inert gas and if appropriate under pressure, or (B/b) initially cyclising with substituted butadienes of the formula (IVb)

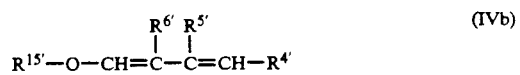

in which

R$^{4'}$, R$^{5'}$ and R$^{6'}$ have the abovementioned meaning and

R$^{15'}$ represents the acetyl or trimethylsilyl radical, in a first step, if appropriate in the presence of a diluent, if appropriate in the presence of a catalyst, if appropriate in the presence of an inert gas and if appropriate under pressure,
and reacting the 2-cyclohexene derivatives thus obtained of the formula (IIc)

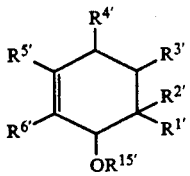 (IIc)

in which
R$^{1'}$ R$^{2'}$, R$^{3'}$, R$^{4'}$, R$^{5'}$ and R$^{6'}$ have the abovementioned meaning and
R$^{15'}$ represents the acetyl or trimethylsilyl radical in a second step, in a generally customary manner, with 4,4'-dimethoxybenzhydrylamine (DMB) of the formula (V)

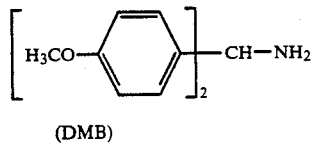 (V)

(DMB)

if appropriate in the presence of a diluent, such as, for example, tetrahydrofuran, at temperatures from 0° C. up to the boiling temperature of the diluent used in each case and in the presence of a catalyst, such as, for example, tetrakis(triphenylphosphine)-palladium(0) of the formula (VI)

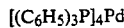 (VI)

[cf. *J. Org. Chem.* 1979, 3451 (1978)]
or
(B/c) reacting the isocyanates intermediately formed according to process (A) of the formula (IIa)

 (IIa)

in which R$^{1'}$, R$^{2'}$, R$^{3'}$, R$^{4'}$, R$^{5'}$ and R$^{6'}$ have the abovementioned meaning
with alcohols of the formula (VII)

 (VII)

in which R$^{16'}$ represents alkyl, alkenyl, alkinyl or alkoxyalkyl having 1 to 12 carbon atoms (preferably 1 to 6 carbon atoms), which is in each case straight-chain or branched and optionally substituted by halogen; or unsubstituted or substituted phenyl or benzyl,
or
(B/d) the substituted 2-cyclohexene derivatives of the formula (IIb) are obtained when the 2-cyclohexene derivatives obtainable by processes (B/a), (B/b) or (B/c) of the formula (IId),

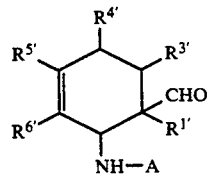 (IId)

in which R$^{1'}$, R$^{3'}$, R$^{4'}$, R$^{5'}$ and R$^{6'}$ and A have the abovementioned meaning, are reduced in a generally customary manner using a complex metal hydride, such as, for example, sodium borohydride, in a suitable solvent, such as, for example, alcohols, such as methanol, ethanol, butanol or isopropanol, and ethers, such as, for example, diethyl ether or tetrahydrofuran, at temperatures from 0° C. to 20° C. and the 2-cyclohexen-1-yl-amine alcohols of the formula (IIe) obtainable in this manner

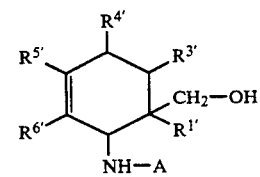 (IIe)

in which R$^{1'}$, R$^{3'}$, R$^{4'}$, R$^{5'}$, R$^{6'}$ and A have the abovementioned meaning, are converted, for example into esters and ethers, by further reactions on the hydroxyl group. Acyl or carbamoyl derivatives of the compounds of the formula (IIb) can furthermore be obtained by reactions with, for example, acyl halides or carbamoyl chlorides,
or
(B/e) the substituted 2-cyclohexene derivatives of the formula (IIb) are obtained when the 2-cyclohexene derivatives obtainable by processes (B/a), (B/b) or (B/c), of the formula (IId)

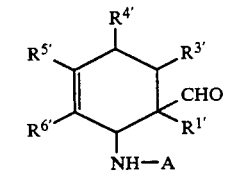 (IIb)

in which R$^{1'}$, R$^{3'}$, R$^{4'}$, R$^{5'}$, R$^{6'}$ and A have the abovementioned meaning, are reacted with alkanephosphonic acid derivatives of the formula (VIII)

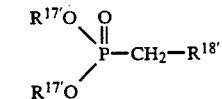 (VIII)

in which
R$^{17'}$ represents methyl or ethyl and
R$^{18'}$ represents the cyano or the alkoxycarbonyl group,
if appropriate in the presence of a diluent, if appropriate in the presence of a base and if appropriate in the presence of an inert gas.

Process (B/a) according to the invention for the preparation of the new 2-cyclohexene derivatives of the formula (IIb) is preferably carried out using diluents.

Suitable diluents here are virtually all the inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as acetonitrile and propionitrile, amides such as, for example, dimethylformamide, dimethylacetamide and N-methylpyrrolidone and also dimethyl sulphoxide, tetramethylene sulphone and hexamethyl phosphoric triamide.

Suitable inert gases in this case are nitrogen and virtually all the rare gases, in particular argon.

The reaction temperatures can be varied within a substantial range in process (B/a) for the preparation of the 2-cyclohexene derivatives of the formula (IIb). In general, the reaction is carried out at temperatures between $-70°$ C. and $+250°$ C., preferably between $-50°$ C. and $+150°$ C.

To carry out process (B/a) for the preparation of the 2-cyclohexene derivatives of the formula (IIb), 1 to 30 mol, preferably 1 to 3 mol of dienophile of the formula (III), 0.01 to 20.0 mol, preferably 0.1 to 5.0 mol of catalyst and, if appropriate, 0.1 to 5 % of a stabiliser preventing free-radical polymerisation, such as, for example, 4-tert-butylcatechol, are in general employed relative to 1 mol of the N-acyl-1-amino-1,3-butadiene derivatives of the formula (IVa).

The process according to the invention for the preparation of the 2-cyclohexene derivatives of the formula (IIb) is in general carried out under elevated pressure. In general, the reaction is carried out at a pressure of 1 to 200 bar, preferably at 5 to 20 bar.

For the preparation of the new 2-cyclohexen-1-ylcarboxylic acid derivatives of the formula (IIb) according to process variant (B/a), suitable catalysts are those customary for reactions of this type; Lewis acids, such as, for example, titanium tetrachloride, tin tetrachloride, aluminium trichloride and boron trifluoride etherate are preferably used.

The process for the preparation of the new 2-cyclohexene derivatives of the formula (IIb) can under certain conditions, however, also be carried out without diluents and a pressure of 1 to 200 bar.

The reactions are in general carried out in a suitable diluent and the reaction mixture is stirred for several hours at the temperature required in each case. Working-up is carried out by customary methods in each case. In general, a procedure is used in which the reaction mixture is either concentrated under reduced pressure or poured into water, and the product is isolated by extraction or filtration and purified by chromatography.

Formula (IVa) provides a general definition of the N-acyl-1-amino-1,3-butadiene derivatives additionally required as starting substances for the preparation of the 2-cyclohexene derivatives of the formula (IIb) according to process variant (B/a). In this formula (IVa), $R^{4'}$, $R^{5'}$, $R^{6'}$ and A represent those radicals which have already been mentioned for these substituents in connection with the description of the compounds of the formula (Ia) according to the invention.

The N-acyl-1-amino-1,3-butadiene derivatives of the formula (IVa) are known and/or can be prepared by methods known from the literature in a simple, analogous manner [cf. *J. Org. Chem.*, 43, 2164 (1978)].

Suitable diluents for carrying out the first step of process (B/b) according to the invention are in this case virtually all the inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoric triamide.

Suitable inert gases in this case are nitrogen and virtually all the rare gases, in particular argon.

The reaction temperatures can be varied within a substantial range when carrying out the first step of process (B/b) according to the invention for the preparation of the 2-cyclohexene derivatives of the formula (IIc). In general, the reaction is carried out at temperatures between $-70°$ C. and $+250°$ C., preferably between $-50°$ C. and $+150°$ C.

To carry out the first step of process (B/b) according to the invention for the preparation of the 2-cyclohexene derivatives of the formula (IIc), 1 to 0.01 mol, preferably 1 to 0.3 mol of the substituted butadienes of the formula (IVb), 0.01 to 20.0 mol, preferably 0.1 to 5.0 mol of catalyst and, if desired, 0.1 to 5 % of a stabiliser preventing free-radical polymerisation, such as, for example, 4-tert-butylcatechol are in general employed relative to 1 mol of the dienophile of the formula (III).

The first step of the process according to the invention for the preparation of the 2-cyclohexene derivatives of the formula (IIc) is in general carried out at elevated pressure. In general, the reaction is carried out at a pressure of 1 to 200 bar, preferably at a pressure of 1 to 20 bar.

For the first step of the process (B/b) according to the invention for the preparation of the new 2-cyclohexene derivatives of the formula (IIc), suitable catalysts are those customary for reactions of this type; Lewis acids, such as, for example, titanium tetrachloride, tin tetrachloride, aluminium trichloride and boron trifluoride etherate are preferably used.

The first step of process (B/b) according to the invention for the preparation of the new 2-cyclohexene derivatives of the formula (IIc) can under certain conditions, however, also be carried out without diluents and a pressure of 1 to 200 bar.

The reactions are in general carried out in a suitable diluent and the reaction mixture is stirred for several hours at the temperature required in each case. Working-up is carried out by customary methods in each case. In general, a procedure is used in which the reaction mixture is either concentrated under reduced pressure or poured into water, and the product is isolated by extraction or filtration and purified by chromatography.

Formula (IVb) provides a general definition of the butadienes additionally required as starting substances for the preparation of the 2-cyclohexene derivatives of the formula (IIc). In this formula (IVb), $R^{4'}$, $R^{5'}$ and $R^{6'}$ represent those radicals which have already been mentioned for these substituents in connection with the description of the compounds of the formula (Ia) according to the invention.

The substituted butadienes of the formula (IVb) are known and/or can be prepared by methods known from the literature in a simple, analogous manner [cf. *J. Org. Chem.*, 30, 2414 (1965)].

The 4,4'-dimethoxybenzhydrylamine (DMB) of the formula (V) and tetrakis(triphenylphosphine)-palladium(0) of the formula (VI) additionally required as starting substances for the second step of process (B/b) according to the invention are generally known compounds of organic chemistry (cf. *J. ,Chem. Soc.*, 7285 (1965)].

Formula (VII) provides a general definition of the alcohols required as starting substances for carrying out process (B/c) according to the invention and which are generally known compounds of organic chemistry.

Process (B/e) according to the invention for the preparation of the new 2-cyclohexene derivatives of the formula (IIb) is preferably carried out using diluents.

Suitable diluents here are virtually all the inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as acetonitrile and propionitrile, amides such as, for example, dimethylformamide, dimethylacetamide and N-methylpyrrolidone and also dimethyl sulphoxide, tetramethylene sulphone and hexamethylphosphoric triamide.

Suitable inert gases in this case are nitrogen and virtually all the rare gases, in particular argon.

The reaction temperatures can be varied within a substantial range in process (B/e) for the preparation of the new 2-cyclohexene derivatives of the formula (IIb). In general, the reaction is carried out at temperatures between $-70°$ C. and $+150°$ C., preferably between $-50°$ C. and $+100°$ C.

Process (B/e) for the preparation of the new 2-cyclohexene derivatives of the formula (IIb) is in general carried out at normal pressure. Under certain conditions, however, it can also carried out at elevated or reduced pressure.

For carrying out process (B/e) for the preparation of the new 2-cyclohexene derivatives of the formula (IIb), in general 1 to 5 mol, preferably 1 to 2 mol, of the alkanephosphonic acid derivatives of the formula (VIII) are in general employed relative to 1 mol of the 2-cyclohexen-1-yl-amine derivatives of the formula (IId).

Bases which can be employed in process (B/e) according to the invention are all the acid-binding agents which can customarily be used for reactions of this type. Those which are preferably suitable are alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium methoxide or ethoxide and potassium methoxide or ethoxide, thallium methoxide or ethoxide, hydrides such as, for example, sodium hydride, and in addition aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO).

The reactions are in general carried out in a suitable diluent in the presence of an acid acceptor and the reaction mixture is stirred for several hours at the temperature required in each case. Working-up is carried out in the process according to the invention by customary methods in each case.

Formula (VIII) provides a general definition of the alkanephosphonic acid derivatives required as starting substances for carrying out process (B/e) for the preparation of the new 2-cyclohexene derivatives of the formula (IIb), which alkanephosphonic acids are known and/or can be prepared by methods known from the literature in a simple, analogous manner.

The compounds of the formula (Ia), (II) and (IIa) to (IIe) can be obtained as enantiomeric or diastereomeric mixtures.

The invention includes both the pure isomers and the mixtures. These mixtures of diastereomers can be separated into the components by customary methods, for example by selective crystallisation from suitable solvents or chromatography on silica gel or alumina. Racemates can be separated into the individual enantiomers by customary methods, i.e., for example, by salt formation with optically active acids such as camphorsulphonic acid or dibenzoyltartaric acid and selective crystallisation, or by derivatisation with suitable optically active reagents, separation of the diastereomeric derivatives and recleavage or separation on optically active column material.

For the preparation of acid addition salts of the compounds of the formula (I), those acids are preferably suitable which have already been mentioned as preferred acids in connection with the description of the acid addition salts according to the invention.

The acid addition salts of the compounds of the formula (I) can be obtained in a simple manner by customary salt formation methods, for example by dissolving a compound of the general formula (I) in a suitable inert solvent and adding the acid, for example hydrochloric acid, and are isolated in a known manner, for example by filtering off, and, if desired, are purified by washing with an inert organic solvent.

For the preparation of metal salt complexes of the compounds of the general formula (I), suitable salts are preferably those salts of metals which have already been described further above.

The metal salt complexes of compounds of the general formula (I) can be obtained in a simple manner by customary methods, i.e., for example, by dissolving the metal salt in alcohol, for example ethanol, and adding it to compounds of the general formula (I). Metal salt complexes can be purified in a known manner, for example by filtering off, isolating and, if desired, purified by recrystallisation.

The compounds of the formula (I) according to the invention and their acid addition salts exhibit antimicrobial, in particular strong antibacterial and antimycotic, actions. They possess a very broad spectrum of antimycotic action, in particular against dermatophytes and Blastomycetes and also biphasic fungi, for example against Candida species, such as Candida albicans, Epidermophyton species, such as Epidermophyton floccosum, Aspergillus species, such as Aspergillus niger and Aspergillus fumigatus, Trichophyton species, such as Trichophyton mentagrophytes, Microsporon species, such as Microsporon felineum and also Torulopsis species, such as Torulopsis glabrata. The enumeration of these microorganisms in no case represents a limitation of the controllable bacteria, but is only of illustrative character.

Examples of indications in human medicine which may be mentioned are: dermatomycoses and systemic mycoses produced by Trichophyton mentagrophytes and other Trichophyton species, Microsporon species and also Epidermophyton floccosum, Blastomycetes and biphasic fungi and also Hyphomycetes.

Indication areas which may be mentioned for example in animal medicine are: all dermatomycoses and systemic mycoses, in particular those which are produced by the abovementioned pathogens.

The present invention includes pharmaceutical preparations which contain one or more active compounds according to the invention or which consist of one or more active compounds according to the invention in addition to non-toxic, inert pharmaceutically suitable excipients.

The present invention also includes pharmaceutical preparations in dosage units. This means that the preparations are in the form of individual portions, for example tablets, coated tablets, capsules, pills, suppositories and ampoules, whose active compound content corresponds to a fraction or a multiple of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half or a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powder or sprays.

Tablets, coated tablets, capsules, pills and granules may contain the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i) in addition to the active compound(s).

The tablets, coated tablets, capsules, pills and granules may be provided with the customary optional opacifying agent-containing coatings and shells and may be so composed that they release the active compound(s), if appropriate with a delay, only or preferably in a certain part of the intestinal tract, in which case, for example, polymeric substances and waxes can be used as embedding materials.

If appropriate the active compound(s) may also be present in microencapsulated form with one or more of the abovementioned excipients.

Suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances, in addition to the active compound(s).

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound(s).

Powders and sprays may contain the customary excipients, for example lactose, talc, silica, aluminium hydroxide, calcium silicate and polyamide powder or mixtures of these substances, and sprays may additionally contain the customary propellants, for example chlorofluorohydrocarbons in addition to the active compound(s).

Solutions and emulsions may contain the customary excipients, such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and bloodisotonic form.

Suspensions may contain the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances in addition to the active compound(s).

The said formulation forms may also contain colorants, preservatives and also odour-improving and flavour-improving additives, for example peppermint oil and eucalyptus oil and sweeteners, for example saccharin.

The therapeutically active compounds should preferably be present in the abovementioned pharmaceutical preparations in a concentration of about 0.1 to 99.5, preferably 0.5 to 95% by weight, of the total mixture.

The abovementioned pharmaceutical preparations may also contain further pharmaceutical active compounds in addition to the active compounds according to the invention.

The production of the abovementioned pharmaceutical preparations takes place in a customary manner by known methods, for example by mixing the active compound(s) with the excipient(s).

The present invention also includes the use of the active compounds according to the invention, and also of pharmaceutical preparations which contain one or more active compounds according to the invention, in human and veterinary medicine for the prophylaxis, amelioration and/or cure of the abovementioned diseases.

The active compounds or the pharmaceutical preparations may be administered locally, orally, parenterally, intraperitoneally and/or rectally, preferably parenterally, in particular intravenously.

In general, it has proven advantageous both in human and veterinary medicine to administer the active compound(s) according to the invention in total amounts of about 2.5 to about 200, preferably 5 to 150 mg/kg of body weight every 24 hours, if appropriate in the form of several individual doses, to obtain the desired results.

For oral administration, the active compounds according to the invention are administered in total amounts of about 2.5 to about 200, preferably 5 to 150 mg/kg of body weight every 24 hours and for parenteral administration in total amounts of about 2.5 to 50, preferably 1 to 25 mg/kg of body weight every 24 hours.

It may be necessary, however, to deviate from the said dosages, depending upon the species and the body weight of the subject to be treated, the nature and severity of the disease, the type of the preparation and the administration of the medicament and also the period or interval within which the administration takes place. Thus, in some cases it may be sufficient to manage with less than the abovementioned amount of active compound, whereas in other cases the abovementioned amount of active compound must be exceeded. The optimum dosage required in each case and the manner of administration of the active compounds can easily be established by one skilled in the art on the basis of his expert knowledge.

PREPARATION EXAMPLES

Example 1

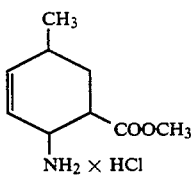

(I-1)

Process A

A solution of 10 g (0.05 mol) of methyl 2-carboxy-5-methylcyclohex-3-ene-carboxylate and 8 g (0.062 mol) of N,N-diisopropyl-ethylamine in 30 ml of acetone is treated over the course of 30 minutes at −5° C. with a solution of 5.4 g (0.05 mol) of ethyl chloroformate in 15 ml of acetone. After a further 30 minutes at 0° C., an ice-cold solution of 6.5 g (0.1 mol) of sodium azide in 15 ml of water is added dropwise. The mixture is stirred at 0° C. for 15 minutes and then worked up using water/toluene.

The organic phase obtained after drying and concentrating to a residual volume of about 50 ml is added dropwise to 50 ml of boiling toluene and the course of the reaction is followed by IR spectroscopy. After complete rearrangement to the isocyanate, the mixture is concentrated, the residue is taken up in 50 ml of tetrahydrofuran and 50 ml of 1N hydrochloric acid and the solution is stirred at 40° C. for 10 hours.

After complete concentration under reduced pressure, 2.8 g (30 % of theory) of 4-methyl-6-carbomethoxy-2-cyclohexen-1-yl-amine hydrochloride are obtained.

$^1$H-NMR data*) (DMSO, 200 MHz): δ=1.00 (3H), 1.50–1.70 ($^1$H), 1.85–2.00 and 2.15–2.35 (2H), 2.85–3.00 (1H), 3.68 (3H), 3.80–3.85 (2H), 5.70–5.90 (2H).

*) The $^1$H-NMR spectra were recorded in dimethyl sulphoxide (DMSO) using tetramethylsilane (TMS) as the internal standard. The chemical shift is given as the δ-value in ppm.

Example 2

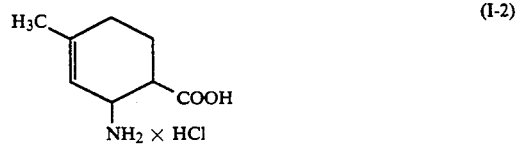

(I-2)

Process B 2 g (7.8 mmol) of tert-butyl (3-methyl-6-carboxy-2-cyclohexen-1-yl)-carbamate are added to 5 ml of 1N hydrochloric acid. After 4 hours at 50° C., the mixture is concentrated to dryness and 1.3 g (87 % of theory) of 3-methyl-6-carboxy-2-cyclohexen-1-yl-amine hydrochloride are obtained as a white solid of melting point 156°–163° C.

The final products of the formula (I)

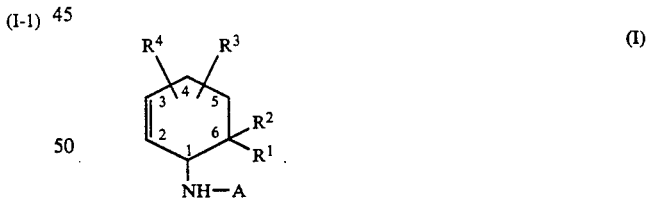

(I)

shown in Table 1 which follows are obtained in an analogous manner to the methods described in Examples 1 and 2 and taking account of the information in the descriptions for the process according to the invention:

TABLE 1

| Ex. No. | R¹ | R² | R³ | R⁴ | A | Physical constants |
|---|---|---|---|---|---|---|
| I-3 | H | COOH | H | 4-CH$_3$ | H | m.p.: 190-193° C. × HCl/homogeneous cis-cis-diastereomer |
| I-4 | H | COOH | H | H | H | m.p.: 169-172° C. × HCl/homogeneous cis-cis-diastereomer |
| I-5 | H | COOCH$_3$ | H | H | H | $^1$H-NMR*(CDCl$_3$, 200 MHz): δ=1.65-2.20(6H), 2.57-2.68(1H), 3.60-3.70(2H), 3.71(3H), 5.78(2H) |
| I-6 | H | COOH | H | 3,4-(CH$_2$—CH$_2$—CH$_2$—CH$_2$)— | H | m.p.: 185-205° C. × HCl |
| I-7 | H | COOCH$_3$ | H | H | H | $^1$H-NMR*(CDCl$_3$, 200 MHz): δ=1.90-2.44(4H), 3.03-3.17 (1H), 3.78(3H), 4.20(1H), 6.00(2H), 8.25-9.65(3H) × HCl |
| I-8 | H | COOH | H | (phenyl, 4-) | H | m.p.: 175-190° C. × HCl |
| I-9 | H | COOCH$_3$ | H | (phenyl, 4-) | H | $^1$H-NMR*(DMSO, 200 MHz): δ=2.75-2.85(1H), 3.30-3.43 (1H), 3.65 and 3.68(3H), 5.75-6.00(2H), 7.10-7.40(5H) |
| I-10 | H | COOCH$_2$CH$_2$OCH$_3$ | H | 4-CH$_3$ | H | $^1$H-NMR*(DMSO, 200 MHz): δ=1.05(3H), 3.30(3H), 5.75-5.95(2H), 8.10-8.50(3H) × HCl |
| I-11 | H | COOH | H | 4-C$_3$H$_7$ | H | m.p.: 180-185° C. × HCl |
| I-12 | Cl | COOH | H | 4-CH$_3$ | H | m.p.: 208-214° C. × HCl |
| I-13 | H | COOH | H | 4-C$_2$H$_5$ | H | m.p.: 168-178° C. × HCl |
| I-14 | H | COOH | H | 3-C$_2$H$_5$ | H | m.p.: 140-150° C. × HCl |
| I-15 | CH$_3$ | COOCH$_3$ | H | H | H | $^1$H-NMR*(DMSO, 200 MHz): δ=1.16 and 1.29(Isomere 3H), 3.65(3H), 5.60-5.70 and 5.85-6.00(2H), 8.20-8.50 (3H)/× HCl |
| I-16 | H | COOH | H | 3-C$_4$H$_9$ | H | m.p.: 180-188° C. × HCl |
| I-17 | H | CN | H | 4-CH$_3$ | H | $^1$H-NMR*(DMSO, 200 MHz): δ=1.05(3H), 1.80-2.10 u, 2.20-2.40(3H), 3.48(1H), 3.95(1H), 5.65-5.95(2H), 8.60-9.00(3H)/× HCl |
| I-18 | H | CN | H | 4-C$_2$H$_5$ | H | m.p.: 130-135° C. × HCl |
| I-19 | Cl | CN | H | 4-CH$_3$ | H | $^1$H-NMR(CDCl$_3$, 200 MHz): δ=1.15(3H), 1.20-1.40 u, 1.85-2.55(5H), 3.60(1H), |

TABLE 1-continued

| Ex. No. | R¹ | R² | R³ | R⁴ | A | Physical constants |
|---|---|---|---|---|---|---|
| I-20 | H | $NO_2$ | phenyl | 4-$CH_3$ | H | m.p.: 215–221° C. × HCl; 5.60–5.85(2H) |
| I-21 | H | —CH=CH—C(=O)—$OC_2H_5$ | H | 4-$CH_3$ | H | ¹H-NMR*)($CDCl_3$, 200 MHz): δ=1.02(3H), 1.29(3H), 4.18(2H), 5.55–6.00(3H), 6.83–7.10(1H), |
| I-22 | H | —CH=CH—COOH | H | H | H | m.p.: 186–218° C. × HCl |
| I-23 | H | —CH=CH—C(=O)—$OC_2H_5$ | H | 4-$CH_3$ | H | m.p.: 191–214° C. × HCl |
| I-24 | H | —$CH_2$—OH | H | 4-$CH_3$ | H | m.p.: 71–83° C. × HCl |
| I-25 | H | | 6,5-(C(=O)—N(C(=O)—)-phenyl) | 4-phenyl | H | m.p.: 51–53° C. × $CF_3COOH$ |
| I-26 | H | | 6,5-(C(=O)—N(C(=O)—)-phenyl) | 4-$CH_3$ | H | m.p.: 80–83° C. × $CF_3COOH$ |
| I-27 | H | | 6,5-(C(=O)—N(C(=O)—)-phenyl) | H | H | m.p.: 75–81° C. × $CF_3COOH$ |
| I-28 | H | —$CH_2O$—$COCH_3$ | H | 4-$CH_3$ | H | ¹H-NMR*)($CDCl_3$, 200 MHz): δ=1.08(3H), 2.10(3H), 4.02–4.28(2H), 5.76–6.00 |

TABLE 1-continued

| Ex. No. | R¹ | R² | R³ | R⁴ | A | Physical constants |
|---|---|---|---|---|---|---|
| I-27 | H | —CO—N(CH$_3$)$_2$ | H | H | H | (2H), 8.10-8.55(3H) × HCl<br>IR: 3500-3350, 1655 cm$^{-1}$ |
| I-30 | H | —CO—N(CH$_3$)$_2$ | H | H | H | IR: 1670 cm$^{-1}$ × CF$_3$COOH |
| I-31 | H | —CO—N(CH$_3$)$_2$ | H | 4-CH$_3$ | H | IR: 1670 cm$^{-1}$ × CF$_3$COOH |
| I-32 | H | —CO—NH— | H | 4-CH$_3$ | H | m.p.: 111-127° C. |
| I-33 | H | —CO—OCH(CH$_3$)$_2$ | H | 4-CH$_3$ | H | $^1$H-NMR*(CDCl$_3$, 200 MHz): δ=1.05(3H), 1.26(6H), 5.08(1H), 5.53-5.80(2H) |
| I-34 | H | —CO—CH$_2$— | H | 4-CH$_3$ | H | $^1$H-NMR*(CDCl$_3$, 200 MHz): δ=1.05(3H), 5.18(2H), 5.60-5.85(2H), 7.25-7.40(5H) |
| I-35 | F | COOH | H | 4-CH$_3$ | H | $^1$H-NMR*(CDCl$_3$, 200 MHz): δ=1.16(3H), 1.80-2.60(3H), 3.83-4.00(1H), 5.65-5.78 u, 6.00-6.13(2H) |
| I-36 | H | —COO—C$_4$H$_9$-n | H | 4-CH$_3$ | H | $^1$H-NMR*(DMSO, 200 MHz): δ=0.89(3H), 1.03(3H), 2.84-2.98(1H), 4.00-4.20(2H), 5.70-5.90(2H), 8.10-8.40(3H) |
| I-37 | H | —COOC$_4$H$_9$-n | H | 4-CH$_3$ | H | IR: 3500-3410, 1735 cm$^{-1}$ |
| I-38 | H | —COOC$_2$H$_5$ | H | 4-CH$_3$ | H | IR: 3500-3400, 1735 cm$^{-1}$ |
| I-39 | H | CN | H | 4-C$_2$H$_5$ | H | $^1$H-NMR*(CDCl$_3$, 200 MHz): δ=0.92(3H), 1.27-1.70(5H), 1.90-2.10(2H), 2.78-2.88 (1H), 3.53-3.60(1H), 5.65-5.80(2H) |
| I-40 | H | —CH$_2$OH | H | 4-CH$_3$ | H | MS: m/e (rel int.): 141(7), 99(32), 83(100) |
| I-41 | H | —CH$_2$OH | H | H | H | $^1$H-NMR*(DMSO, 200 MHz): δ=1.30-2.10(5H), 5.63-5.82 u, 5.90-6.08(2H), 8.00-8.40(3H) |
| I-42 | H | —COOH | H | 5-CH(CH$_3$)$_2$ | H | m.p.: 189-205° C./× HCl |
| I-43 | H | —COOH | H | 4-CH$_3$ | H | m.p.: 130-138° C. diastereomer ratio 70:30/× HCl |

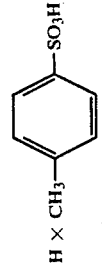

TABLE 1-continued

| Ex. No. | R¹ | R² | R³ | R⁴ | A | Physical constants |
|---|---|---|---|---|---|---|
| I-55 | H | —COOH | H | 4-CH₃ | H × CH₃CO₂H | ¹H-NMR(DMSO): δ = 0.95(3H); 1.85(3H); 5.60–5.80(2H). |
| I-56 | H | —COOH | H | 4-CH₃ | H × HCl | isomer to I-3 ¹H-NMR(CD₃OD): δ = 1.06(3H); 1.83(1H); 2.00(1H); 2.38 (1H); 2.81(1H); 4.08(1H); 5.60(1H); 6.00(1H). |
| I-57 | H | —CH₂—OH | H | 4-CH₃ | H × HCl | ¹H-NMR(DMSO): δ = 1.00 (3H); 3.45(2H); 5.70–5.90 (2H); 8.06(3H). |
| I-58 | H | —COOH | H | 4-CH₃ | H (zwitterion) | Fp.: 208–211° C. |
| I-59 | H | —CO₂CH₃ | H | 4-CH₃ | ![saccharin structure] | strongly hygroscopic |
| I-60 | H | —CO₂CH₃ | H | 4-CH₃ | H × HO₂CCH₂C(OH)—(CO₂H)CH₂CO₂H | hygroscopic |
| I-61 | H | —CO₂CH₃ | H | 4-CH₃ | H × HO₂CCO₂H | m.p.: 152–158° C. |
| I-62 | H | —CO₂CH₃ | H | 4-CH₃ | ![toluenesulfonic acid] H × HO₃S—C₆H₄—CH₃ | m.p.: 125–128° C. |
| I-63 | H | —CO₂CH₃ | H | 4-CH₃ | H × CH₃CO₂H | m.p.: 89.5–90° C. |
| I-64 | H | —CO₂(CH₂)₂OCH₃ | H | 4-CH₃ | H | $n_D^{20}$ 1,4763 |
| I-65 | H | —CO₂CH₃ | H | 4-CH₃ | H | $n_D^{20}$ 1,4791 |
| I-66 | H | —CO₂H | H | 4-CH₃ | ![saccharin structure] | ¹H-NMR(DMSO): δ = 1.00(3H), 1.50(1H); 2.00(2H); 2.30 (1H); 2.85(1H); 3.90(1H); 5.60–5.95(2H); 7.61(5H). |
| I-67 | H | —CO₂H | H | 4-CH₃ | H × HO₂CCO₂H | ¹H-NMR(DMSO): δ = 1.05(3H), 1.45(1H); 2.05 (1H); 2.31(1H); 2.85(1H); 3.80(1H); 5.60–5.80(2H). |

TABLE 1-continued

| Ex. No. | $R^1$ | $R^2$ | $R^3$ | $R^4$ | A | Physical constants |
|---|---|---|---|---|---|---|
| I-68 | H | —CO$_2$(CH$_2$)$_3$CH$_3$ | H | 4-CH$_3$ | (structure: 2-aminosulfonyl-benzoyl, H×HN-SO$_2$-C$_6$H$_4$-C(=O)-) | waxy solid |
| I-69 | H | —CO$_2$CH$_2$CH(CH$_3$)$_2$ | H | 4-CH$_3$ | H | $^1$H-NMR(CDCl$_3$): δ = 0.90–1.08(9H); 2.60–2.73(1H); 3.90(2H); 5.60–5.80(2H). |
| I-70 | H | —CO$_2$CH$_2$CH(CH$_3$)$_2$ | H | 4-CH$_3$ | H × HCl | $^1$H-NMR(DMSO): δ = 0.85–1.05(9H); 2.90–3.00(1H); 3.90(2H); 5.70–5.90(2H); 5.20(3H). |
| I-71 | H | —CO$_2$H | H | 4-CH$_3$ | H × Cu(OAc)$_2$ | MS (FAB): 155 [M$^+$-Cu(Ac)$_2$] |
| I-72 | H | —CO$_2$H | H | 4-CH$_3$ | H × HO$_2$CCH$_2$CO$_2$H | MS (FAB): 259 [M$^+$] |
| I-73 | H | —CO$_2$H | H | 4-CH$_3$ | H × HO$_2$C—CH=CH—CH=CH—CH$_3$ | MS (FAB): 267 [M$^+$] |
| I-74 | H | —CO$_2$H | H | CH(CH$_3$)$_2$ | zwitterion | m.p.: 203–206° C. (dec.) |
| I-75 | H | —CO$_2$H | H | H | H | m.p.: 98° C. |
| I-76 | H | —CO$_2$H | 3-CH$_3$ | 4-CH$_2$CH$_2$(CH$_3$)$_2$ | H | m.p.: 133–135° C. |
| I-77 | H | —CO$_2$H | 3-C$_6$H$_5$ | 4-CH$_3$ | H | m.p.: 140–145° C. |
| I-78 | H | —CO$_2^-$ Na$^+$ | H | 4-CH$_2$CH$_2$(CH$_3$)$_2$ | H | m.p.: >250° C. (decomposition) |
| I-79 | H | —CO$_2^-$ NH$_4^+$ | H | 4-CH$_3$ | H | m.p.: >250° C. (decomposition) |
| I-80 | H | —CO$_2$CH$_3$ | 3-C$_6$H$_5$ | 4-CH$_2$CH(CH$_3$)$_2$ | H | $^1$H-NMR(CDCl$_3$): δ = 0.75–0.95(9H); 2.65–2.85(1H); 3.75(3H); 5.90(1H); 7.15–7.40(5H). |
| I-81 | H | —CO$_2$H | H | H | H × HO$_2$CCO$_2$H | Fp.: 147–150° C. (decomposition) |
| I-82 | H | —CO$_2$H | H | H | (structure: 2-methyl-benzenesulfonamido-acetyl, H×HN-SO$_2$-C$_6$H$_4$(CH$_3$)-C(=O)-) | Fp.: 106–112° C. (decomposition) |
| I-83 | H | —CO$_2$H | 3-C$_6$H$_5$ | 4-CH(CH$_3$)$_2$ | H × HCl | m.p.: 245–248° C. |
| I-84 | H | —CO$_2$H | 3-CH(CH$_3$)$_2$ | 4-CH$_2$CH(CH$_3$)$_2$ | H × HCl | m.p.: 210–218° C. |
| I-85 | H | —CN | 3-CH(CH$_3$)$_2$ | 4-CH$_2$CH(CH$_3$)$_2$ | H × HCl | m.p.: 164° C. |
| I-86 | H | —CN | 3-C$_6$H$_5$ | 4-CH(CH$_3$)$_2$ | H × HCL | m.p.: 233–261° C. |
| I-87 | H | —CO$_2$C$_2$H$_5$ | H | H | H × HCl | m.p.: 139–148° C. |
| I-88 | H | —CO$_2$CH(CH$_3$)$_2$ | H | H | H × HCl | m.p.: 188–188.5° C. |
| I-89 | H | —CO$_2$C$_6$H$_5$ | H | 4-CH$_3$ | H × HCl | m.p.: 117° C. |
| I-90 | H | —CO$_2$C$_6$H$_5$ | H | 4-CH$_3$ | H × HCl | $^1$H-NMR(DMSO) δ = 1.00 (3H); 1.40(1H); 2.80(1H); |

TABLE 1-continued

| Ex. No. | $R^1$ | $R^2$ | $R^3$ | $R^4$ | A | Physical constants |
|---|---|---|---|---|---|---|
| I-91 | H | —CO$_2$CH$_3$ | H | 4-CH(CH$_3$)$_2$ | H × HCl | 5.65–5.95(2H); 7.20(5H). MS: 197 [M$^+$ − HCl] |
| I-92 | H | —CO$_2$CH$_3$ | H | 4-CH$_3$ | H × HCl | MS: 231 [M$^+$ − 183] |
| I-93 | H | —CO$_2$H | H | H | H × HCl | (+) enantiomer of I-4 m.p.: 210–213.5° C. |
| I-94 | H | —CO$_2$H | H | H | H × HCl | (−) enantiomer of I-4 m.p.: 208–210° C. |
| I-95 | H | —CO$_2$H | H | 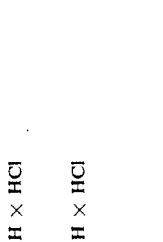 | H × HCl | MS: M$^+$ of 207 by FAB-spectroscopy |
| I-96 | H | —CO$_2$CH$_3$ | H | H | H × HCl | enantiomer MS (FAB): 191 [M$^+$] |
| I-97 | H | —CO$_2$CH$_3$ | H | H | H × HCl | enantiomer MS (FAB): 191 [M$^+$] |
| I-98 | H | CO$_2$CH$_2$—C$_6$H$_5$ | H | H | H | $^1$H-NMR(CDCl$_3$): δ = 1.50 (2H); 2.60–2.70(1H); 3.67 (1H); 5.15(2H); 5.75(2H); 7.32(5H). |
| I-99 | H | CO$_2$CH$_2$-2,4-Cl$_2$C$_6$H$_3$ | H | 4-CH$_3$ | H | $^1$H-NMR(CDCl$_3$): δ = 1.05 (d, 3H); 2.73–2.85(1H); 5.22(2H); 5.78(2H); 7.22–7.40(3H). |
| I-100 | H | CO$_2$CH$_2$—C$_6$H$_5$ | H | H | H × HCl | MS: 231 [M$^+$ − 36] |
| I-101 | H | CO$_2$CH$_2$-2,4-Cl$_2$C$_6$H$_3$ | H | 4-CH$_3$ | H × HCl | MS: 313 [M$^+$ − 36] |
| I-102 | H | CO$_2$CH$_2$-2-ClC$_6$H$_4$ | H | 4-CH$_3$ | H | $^1$H-NMR(CDCl$_3$): δ = 1.05 (3H); 2.60(2H); 2.65–2.77 (1H); 5.26(2H); 5.56–5.80 (2H); 7.20–7.50(4H). |
| I-103 | H | CO$_2$CH$_2$-3-ClC$_6$H$_4$ | H | 4-CH$_3$ | H | $^1$H-NMR(CDCl$_3$): δ = 1.06 (3H); 2.68–2.80(1H); 3.77 (1H); 5.15(2H); 5.60–5.80 (2H); 7.3(4H). |
| I-104 | H | CO$_2$CH$_2$-4-ClC$_6$H$_4$ | H | 4-CH$_3$ | H | $^1$H-NMR(CDCl$_3$): δ = 1.05 (3H); 2.65–2.78(1H); 5.15 (2H); 5.60–5.80(2H); 7.32(4H). |
| I-105 | H | CO$_2$CH$_2$-4-NO$_2$C$_6$H$_4$ | H | 4-CH$_3$ | H × HCl | m.p.: 118–124° C. |
| I-106 | H | CO$_2$CH$_2$-2-ClC$_6$H$_4$ | H | 4-CH$_3$ | H × HCl | MS: 279 [M$^+$ − 36] |
| I-107 | H | CO$_2$CH$_2$-3-ClC$_6$H$_4$ | H | 4-CH$_3$ | H × HCl | MS: 279 [M$^+$ − 36] |
| I-108 | H | CO$_2$CH$_2$-4-ClC$_6$H$_4$ | H | 4-CH$_3$ | H × HCl | m.p.: 167° C. |

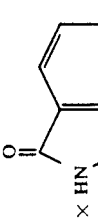

TABLE 1-continued

| Ex. No. | R¹ | R² | R³ | R⁴ | A | Physical constants |
|---|---|---|---|---|---|---|
| I-109 | H | CO$_2$CH$_2$-4-NO$_2$C$_6$H$_4$ | H | 4-CH$_3$ | H × HCl | m.p.: 196-202° C. |
| I-110 | H | CO$_2$CH$_2$-2-ClC$_6$H$_4$ | H | H | H | $^1$H-NMR(CDCl$_3$): δ = 1.80-2.15(4H); 2.65-2.85(3H); 5.29(2H); 5.78(2H); 7.20-7.50(4H). |
| I-111 | H | CO$_2$CH$_2$-3-ClC$_6$H$_4$ | H | H | H | $^1$H-NMR(CDCl$_3$): δ = 1.75-2.15(4H); 2.56(2H); 2.65-2.75(1H); 5.15(2H); 5.79 (2H); 7.20-7.40(4H). |
| I-112 | H | CO$_2$CH$_2$-4-ClC$_6$H$_4$ | H | H | H | m.p.: 142° C. |
| I-113 | H | CO$_2$CH$_2$-4-NO$_2$C$_6$H$_4$ | H | H | H | $^1$H-NMR(CDCl$_3$): δ = 1.75-2.15(6H); 5.28(2H); 5.78 (2H); 7.55(2H); 8.20(2H). |
| I-114 | H | CO$_2$CH$_2$-2-ClC$_6$H$_4$ | H | H | H × HCl | $^1$H-NMR(DMSO): δ = 1.95-2.12(4H); 5.15-5.35(2H); 5.65-6.05(2H); 7.30-7.60 (4H); 8.25(3H). |
| I-115 | H | CO$_2$CH$_2$-3-ClC$_6$H$_4$ | H | H | H × HCl | $^1$H-NMR(DMSO): δ = 1.95-2.12(4H); 3.10(1H); 5.19 (2H); 7.39(4H); 8.25(3H). |
| I-116 | H | CO$_2$CH$_2$-4-ClC$_6$H$_4$ | H | H | H × HCl | MS: 265 [M⁺ — 36] |
| I-117 | H | CO$_2$CH$_2$-4-NO$_2$C$_6$H$_4$ | H | H | H | $^1$H-NMR(DMSO): δ = 1.90-2.15(4H); 5.33(2H); 5.70-6.05(2H); 7.70(2H); 8.20 (2H); 8.45(3H). |
| I-118 | H | CO$_2$CH$_2$-3,5-(OCH$_3$)$_2$C$_6$H$_3$ | H | 4-CH$_3$ | H | $^1$H-NMR(CDCl$_3$): δ = 1.03 (3H); 3.79(6H); 5.10(2H); 5.58-5.80(2H); 6.40-6.55 (3H). |
| I-119 | H | CO$_2$CH$_2$-2-NO$_2$C$_6$H$_4$ | H | 4-CH$_3$ | H | $^1$H-NMR(CDCl$_3$): δ = 1.05 (3H); 5.56(2H); 5.60-5.85 (2H); 7.45-7.70(3H); 8.10 (1H). |
| I-120 | H | CO$_2$CH$_2$-2,4-Cl$_2$C$_6$H$_3$ | H | H | H | $^1$H-NMR(CDCl$_3$): δ = 2.65-2.78(1H); 2.70(1H); 5.21 (2H); 5.78(2H); 7.20-7.35 (3H). |
| I-121 | H | CO$_2$CH$_2$-3-NO$_2$C$_6$H$_4$ | H | H | H | MS: 276 [M⁺] |
| I-122 | H | CO$_2$CH$_2$-3,5-(OCH$_3$)$_2$C$_6$H$_3$ | H | H | H | $^1$H-NMR(CDCl$_3$): δ = 3.79 (6H); 5.10(2H); 5.80(2H); 6.40-6.60(3H). |
| I-123 | H | CO$_2$CH$_2$-3-NO$_2$C$_6$H$_4$ | H | 4-CH$_3$ | H | $^1$H-NMR(CDCl$_3$): δ = 1.05 (3H); 2.68-2.80(1H); 5.28 (2H); 5.55-5.80(2H); 7.50-7.75(2H); 8.15-8.30(2H). |
| I-124 | H | CO$_2$CH$_2$—C$_6$H$_5$ | H | 4-CH(CH$_3$)$_2$ | H | $^1$H-NMR(CDCl$_3$): δ = 0.90 (6H); 2.60-2.70(1H); 5.17 (2H); 5.60-5.85(2H); 7.35 (5H). |
| I-125 | H | CO$_2$CH$_2$-3,5-(OCH$_3$)$_2$C$_6$H$_3$ | H | 4-CH$_3$ | H × HCl | $^1$H-NMR(DMSO): δ = 8.29 (—NH$_3^⊕$, 3H). |
| I-126 | H | CO$_2$CH$_2$-2-NO$_2$C$_6$H$_4$ | H | 4-CH$_3$ | H × HCl | $^1$H-NMR(DMSO): δ = 8.35 |

TABLE 1-continued

| Ex. No. | R¹ | R² | R³ | R⁴ | A | Physical constants |
|---|---|---|---|---|---|---|
| I-127 | H | CO$_2$CH$_2$-2,4-Cl$_2$C$_6$H$_3$ | H | H | H × HCl | (—NH$_3^\oplus$, 3H). $^1$H-NMR(DMSO): δ=8.25 (—NH$_3^\oplus$, 3H). |
| I-128 | H | CO$_2$CH$_2$-3-NO$_2$C$_6$H$_4$ | H | H | H × HCl | $^1$H-NMR(DMSO): δ=8.40 (—NH$_3^\oplus$, 3H). MS: 291 [M⁺ − 36] |
| I-129 | H | CO$_2$CH$_2$-3,5-(OCH$_3$)$_2$C$_6$H$_3$ | H | H | H × HCl | |
| I-131 | H | CO$_2$CH$_2$C$_6$H$_5$ | H | 4-CH(CH$_3$)$_2$ | H × HCl | $^1$H-NMR(DMSO): δ=0.85 (6H); 1.55–2.10(4H); 5.20 (2H); 5.80–6.00(2H); 7.38 (5H); 8.35(3H). |
| I-132 | H | CO$_2$CH$_2$-3,5-Cl$_2$C$_6$H$_3$ | H | H | H | $^1$H-NMR(CDCl$_3$): δ=1.75–2.15(6H); 2.65–2.80(1H); 5.22(2H); 5.78(2H); 7.20–7.50(3H). |
| I-133 | H | CO$_2$CH$_2$-2,6-Cl$_2$C$_6$H$_3$ | H | H | H | $^1$H-NMR(CDCl$_3$): δ=1.75–2.15(6H); 5.40(2H); 5.75 (2H); 7.20–7.40(3H). |
| I-134 | H | CO$_2$CH$_2$-3,5-Cl$_2$C$_6$H$_3$ | H | H | H × HCl | $^1$H-NMR(DMSO): δ=8.43 (—NH$_3^\oplus$, 3H). |
| I-135 | H | CO$_2$CH$_2$-2,6-Cl$_2$C$_6$H$_3$ | H | H | H × HCl | $^1$H-NMR(DMSO): δ=8.25 (—NH$_3^\oplus$, 3H). |
| I-136 | H | COOC$_2$H$_5$ | H | H | —H$_2$C-Ph | $^1$H-NMR: (200 MHz, CDCl$_3$): δ=1.25(t, 3H); 3.85 (d, 2H); 5.70–5.90(m, 2H); 7.30(m, 5H). |
| I-137 | H | COOCH$_3$ | H | H | —CONH$_2$ | Smp.: 236 (decomposition) |
| I-138 | H | COOCH$_3$ | H | H | —COPh | Sup: 92–99 |
| I-139 | H | COOCH$_3$ | H | H | —CHO | $^1$H-NMR: (200 MHz, CDCl$_3$): δ=3.67(s, 3H); 5.60–5.90 (2H); 8.70(s, 1H). |
| I-140 | H | COOCH$_3$ | H | H | —COCH$_3$ | $^1$H-NMR: (200 MHz, DMSO): δ=2.10(s, 3H); 3.60 (s, 3H); 5.60–5.90(2H). |

*)The $^1$H-NMR spectra were recorded in deuterochloroform (CDCl$_3$) or dimethyl sulphoxide (DMSO) using tetramethylsilane (TMS) as the internal standard. The chemical shift is given as the δ-value in ppm.

Preparation of the Starting Substances

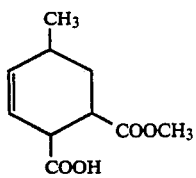
(II)

A solution of 10 g (0.089 mol) of sorbic acid, 24.1 ml (0.27 mol) of methyl acrylate, 0.1 g (0.6 mmol) of 4-tert-butylcatechol and 100 ml of dioxane is reacted at a temperature of 110° C and at 5 bar for 30 hours. The dioxane is distilled off and the residue is separated from the polar by-products using the eluent mixture petroleum ether/ethyl acetate (2:1).

13.2 g (75 % of theory) of methyl 2-carboxy-5-methylcyclohex-3-ene-carboxylate are obtained as an isomer mixture.

$^1$H-NMR*) (CDCl$_3$, 200 MHz): δ=1.05 (d, 3H); 3.65 (s, 3H),
*) The $^1$H-NMR spectra were recorded in deuterochloroform (CDCl$_3$) using tetramethylsilane (TMS) as the internal standard. The chemical shift is given as the ω-value in ppm. 5.40–5.90 (m, 2H).

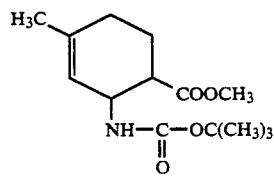
(IIb-1)

Process B/a

A solution of 20.5 g (0.11 mol) of tert-butyl (trans-3-methyl-1,3-butadiene)-1-carbamate, 34 g (0.39 mol) of methyl acrylate, 1 g (6 mmol) of 4-tert-butylcatechol and 90 ml of dioxane is reacted at 110° C. and at 6 bar for 20 hours. After distilling off the excess methyl acrylate, the residue is separated on silica gel using the eluent mixture petroleum ether/ethyl acetate (5:1).

24 g (80 % of theory) of tert-butyl (3-methyl-6-carbomethoxy-2-cyclohexen-1-yl)-carbamate are obtained as a waxy solid.

$^1$H-NMR*) (CDCl$_3$, 200 MHz): δ=1.42 (9H), 1.68 (3H), 1.70–2.00 (4H), 2.70 (1H), 3.68 (3H), 4.50 (1H), 4.80 (1H), 5.30–5.45 (1H).
*) The $^1$H-NMR spectra were recorded in deuterochloroform (CDCl$_3$) using tetramethylsilane (TMS) as the internal standard. The chemical shift is given as the ω-value in ppm.

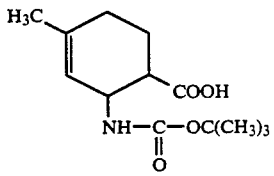
(IIb-2)

5 g (18.6 mmol) of tert-butyl (3-methyl-6-carbomethoxy-2-cyclohexen-1-yl)-carbamate are added to 40 ml of 1N sodium hydroxide solution and the mixture is stirred at 50° C. until the solution has become clear. It is extracted once with diethyl ether and then adjusted to a pH of 1 at 0° C. using concentrated hydrochloric acid. After extraction with diethyl ether and concentration, 3.5 g (74 % of theory) of tert-butyl 3-methyl-6-carboxy-2-cyclohexen-1-yl-carbamate of melting point 132°–136° C. are obtained.

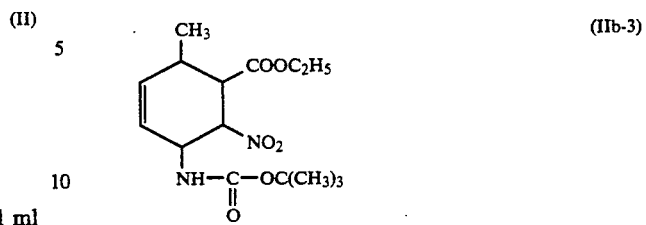
(IIb-3)

Process B/a

A solution of 18.8 g (0.13 mol) of ethyl trans-3-nitroacrylate in 100 ml of benzene is added dropwise at room temperature to a solution of 20.1 g (0.11 mol) of tertbutyl trans-1,3-pentadiene-1-carbamate and 0.25 g (1.5 mmol) of 4-tert-butylcatechol in 50 ml of benzene and the mixture is stirred at room temperature for 20 hours. The solution is concentrated to half its volume and allowed to crystallise out at +4° C.

18.3 g (53 % of theory) of ethyl 3-(N-tert-butyloxycarbonylamino)-2-nitro-6-methyl-4-cyclohexene-carboxylate are obtained of melting point 139°–45° C.

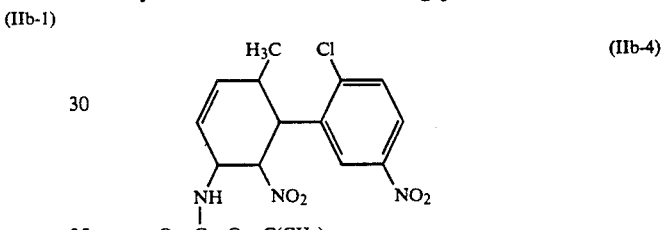
(IIb-4)

Process B/a 10 g (55 mmol) of tert-butyl (trans-1,3-pentadiene)-1-carbamate, 12.4 g (55 mmol) of trans-2-(2-chloro-5-nitrophenyl)-nitroethene and 0.6 g (3.6 mmol) of 4-tert-butylcatechol are reacted at 110° C. at 4 bar for 30 hours in 100 ml of dioxane. The reaction mixture is concentrated and the residue is recrystallised twice from ethanol.

7 g (31 % of theory) of tert-butyl 4-methyl-5-(2-chloro-5-nitro-phenyl)-6-nitro-2-cyclohexen-1-yl-carbamate of melting point 195°–203° C. are obtained.

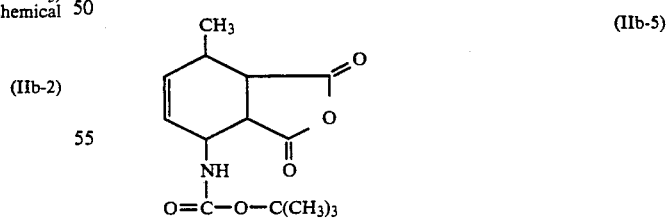
(IIb-5)

Process B/a

A solution of 1 g (5.5 mmol) of tert-butyl trans-1,3-pentadiene-1-carbamate, 1.1 g (11 mmol) of maleic anhydride, 40 mg (0.2 mmol) of 4-tert-butylcatechol and 3 ml of dioxane is heated to 100° C for 2 hours. The mixture is concentrated to dryness and, after recrystallisation from benzene, 0.8 g (52 % of theory) of tert-butyl (4-methylcyclohex-2-ene-5,6-dicarboxylic anhydrid-1- yl)-carbamate is obtained of melting point 180°-182° C.

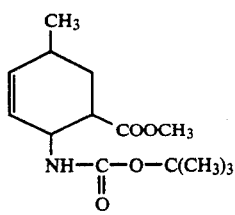

(IIb-6)

Process B/c

A solution of 10 g (0.05 mol) of methyl 2-carboxy-5-methylcyclohex-3-ene-carboxylate and 8 g (0.062 mol) of N,N-diisopropylethylamine in 30 ml of acetone is treated at −5° C. over the course of 30 minutes with a solution of 5.4 g (0.05 mol) of ethyl chloroformate in 15 ml of acetone. After a further 30 minutes at 0° C., an ice-cooled solution of 6.5 g (0.1 mol) of sodium azide in 15 ml of water is added dropwise. The mixture is stirred at 0° C. for 15 minutes and then worked up using water-toluene. The toluene phase which is concentrated to about 50 ml is then added dropwise to a solution of 3 g (0.04 mol) of tert-butanol and 25 mg (0.15 mmol) of tert-butylcatechol in 20 ml of toluene which is boiling under reflux. The course of the reaction is monitored by IR spectroscopy.

The mixture is allowed to cool to room temperature and is concentrated. After separation on silica gel by column chromatography using the eluent petroleum ether/ethyl acetate (6:1), 4 g (30% of theory) of tert-butyl (4-methyl-6-carbomethoxy-2-cyclohexen-1-yl)-carbamate of melting point 89°-91° C. are obtained.

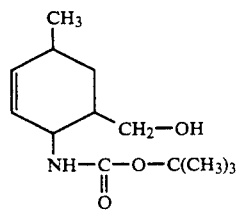

(IIb-7)

Process B/d 5 g (21 mmol) of tert-butyl (4-methyl-6-formyl-2-cyclohexen-1-yl)-carbamate are dissolved in 70 ml of tetrahydrofuran and, after addition of 1.6 g (42 mmol) of sodium borohydride, the mixture is stirred at 55° C. for 15 minutes. 17 ml of methanol are then slowly added dropwise at 55° C. and after addition is complete the mixture is subsequently stirred at room temperature for 3 hours. The mixture is subjected to aqueous work-up, extracted with diethyl ether and, after drying over magnesium sulphate and concentrating, 4.8 g (95 % of theory) of 2-[(tert-butyloxycarbonylamino)-5-methyl-3-cyclohexen-1-yl]-methanol are obtained as a white, waxy solid.

$^1$H-NMR*) (CDCl$_3$, 200 MHz): δ=1.00 (d, 3H), 1.45 (s, 9H), 1.75-2.40 (m, 2H), 3.28-3.52 and 3.67-3.80 (m, 2H), 4.00-4.30 and 4.45-4.75 (m, 2H), 5.43-5.51 and 5.63-5.78 (m, 2H).

*) The $^1$H-NMR spectra were recorded in deuterochloroform (CDCl$_3$) using tetramethylsilane (TMS) as the internal standard. The chemical shift is given as the ω-value in ppm.

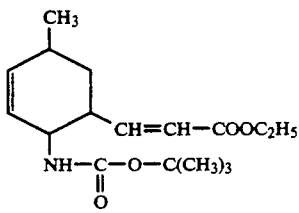

(IIb-8)

Process B/e 24 g (0.105 mol) of triethyl phosphonoacetate are added dropwise at 0° C. to a suspension of 3.4 g (80 % in oil =0.1 mol) of sodium hydride. After completion of the evolution of hydrogen, a solution of 25 g (0.105 mol) of tert-butyl (4-methyl-6-formyl-2-cyclohexen-1-yl)-carbamate in 30 ml of tetrahydrofuran is added dropwise. After stirring at room temperature for 4 hours, the reaction mixture is added to 500 ml of water and extracted several times with ethyl acetate. The combined organic phases are washed with water and saturated sodium chloride solution, dried and concentrated. After purification by column chromatography on silica gel using the eluent petroleum ether/ethyl acetate (5:1), 26 g (80 % of theory) of methyl trans-(2-N-tert-butoxycarbonylamino-4-methyl-cyclohex-2-en-1-yl)-acrylate are obtained.

$^1$H-NMR*) (CDCl$_3$ 200 MHz): δ=1.05 (d, 3H), 1.20-1.35 (m, 3H), 1.43 (s, 9H), 1.60-2.60 (m, 4H), 4.15 (q, 2H), 4.25-4.60 (br. m, 2H), 5.50-5.95 (m, 3H), 6.86-7.10 (m, 1H).

*) The $^1$H-NMR spectra were recorded in deuterochloroform (CDCl$_3$) using tetramethylsilane (TMS) as the internal standard. The chemical shift is given as the δ-value in ppm.

The initial products of the formula (IIb)

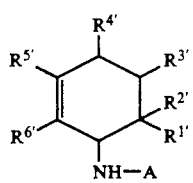

(IIb)

shown in Table 2 which follows are obtained in an analogous manner to the methods described in Examples (IIb-1) to (IIb-8) and taking account of the information in the descriptions for the process according to the invention:

TABLE 2

| Ex. No. | A | R¹' | R²' | R³' | R⁴' | R⁵' | R⁶' | Physical constants |
|---|---|---|---|---|---|---|---|---|
| IIb-9 | $-\overset{\|}{\underset{\|}{C}}-OC(CH_3)_3$, C=O | H | —COOH | H | H | H | H | m.p.: 110–118° C. |
| IIb-10 | $-\overset{\|}{\underset{\|}{C}}-OC(CH_3)_3$, C=O | H | —COOH | H | CH₃ | H | H | m.p.: 194–196° C. |
| IIb-11 | $-\overset{\|}{\underset{\|}{C}}-OC(CH_3)_3$, C=O | H | —COOCH₃ | H | H | H | H | ¹H-NMR*)(CDCl₃, 200 MHz) δ=1.42(9H), 1.70–2.10(4H), 2.73–2.85(1H), 3.68(3H), 4.48–4.59(1H), 4.85–4.95 (1H), 5.60–5.86(2H) |
| IIb-12 | $-\overset{\|}{\underset{\|}{C}}-OC(CH_3)_3$, C=O | H | —COOCH₃ | H | (phenyl) | H | H | ¹H-NMR*)(CDCl₃, 200 MHz) δ=1.44(9H), 1.58–1.78(1H), 2.08–2.20(1H), 3.30–3.40(1H), 3.62(3H), 4.60–4.80(2H), 6.90(2H), 7.12–7.35(5H) |
| IIb-13 | $-\overset{\|}{\underset{\|}{C}}-OC(CH_3)_3$, C=O | H | —COOCH₃ | H | —CH₂—(CH₂)₂—CH₂— | | H | ¹H-NMR*)(CDCl₃, 200 MHz) δ=0.80–2.30(20H), 2.60–2.71(1H), 3.65(3H), 4.50(2H), 5.43(1H) |
| IIb-14 | $-\overset{\|}{\underset{\|}{C}}-OC(CH_3)_3$, C=O | H | —COOH | H | —CH₂—(CH₂)₂—CH₂— | | H | m.p.: 160–168° C. |
| IIb-15 | $-\overset{\|}{\underset{\|}{C}}-OC(CH_3)_3$, C=O | CH₃ | —COOCH₃ | H | H | H | H | ¹H-NMR*)(CDCl₃, 200 MHz) δ=1.18(3H), 1.44(9H), 3.68(3H), 5.50–5.80(2H) |
| IIb-16 | $-\overset{\|}{\underset{\|}{C}}-OC(CH_3)_3$, C=O | H | —CONH₂ | H | CH₃ | H | H | m.p.: 148–150° C. |
| IIb-17 | $-\overset{\|}{\underset{\|}{C}}-OC(CH_3)_3$, C=O | H | —COOCH₃ | H | C₃H₇ | H | H | ¹H-NMR*)(CDCl₃, 200 MHz) δ=0.90(3H), 1.20–1.48(9H), 1.85–2.12(2H), 3.67(3H), 4.52(2H), 5.71(2H) |
| IIb-18 | $-\overset{\|}{\underset{\|}{C}}-OC(CH_3)_3$, C=O | H | —COOCH₃ | H | C₂H₅ | H | H | m.p.: 79–85° C. |
| IIb-19 | $-\overset{\|}{\underset{\|}{C}}-OC(CH_3)_3$, C=O | H | —COOH | H | C₂H₅ | H | H | m.p.: 149–167° C. |

TABLE 2-continued

| Ex. No. | A | R¹' | R² | R³' | R⁴' | R⁵' | R⁶' | Physical constants |
|---|---|---|---|---|---|---|---|---|
| IIb-20 | —C(=O)—OC(CH₃)₃ | H | —COOH | H | H | n-C₄H₉ | H | ¹H-NMR*(CDCl₃, 200 MHz) δ=0.89(3H), 1.10–1.50 u, 1.80–2.00(20H), 2.70–2.85(1H), 4.40–4.60 u, 5.00–5.20(1H), 5.35(2H) |
| IIb-21 | —C(=O)—OC(CH₃)₃ | H | —COOH | H | H | C₂H₅ | H | m.p.: 120–128° C. (hygroscopic) |
| IIb-22 | —C(=O)—OC(CH₃)₃ | H | —COOCH₃ | H | H | C₂H₅ | H | m.p.: 65–71° C. |
| IIb-23 | —C(=O)—OC(CH₃)₃ | H | —COOH | H | C₃H₇ | H | H | m.p.: 116–142° C. |
| IIb-24 | —C(=O)—OC(CH₃)₃ | H | —CN | H | C₂H₅ | H | H | m.p.: 121–122° C. |
| IIb-25 | —C(=O)—OC(CH₃)₃ | H | —CN | H | CH₃ | H | H | MS: 183 M⁺(12), 153, 127, 83, 57(100) |
| IIb-26 | —C(=O)—OC(CH₃)₃ | Cl | —CN | H | CH₃ | H | H | m.p.: 116–121° C. |
| IIb-27 | —C(=O)—OC(CH₃)₃ | H | —NO₂ | —COOC₂H₅ | H | H | H | m.p.: 95–96° C. |
| IIb-28 | —C(=O)—OC(CH₃)₃ | H | —NO₂ | 3-NO₂-C₆H₄ | CH₃ | H | H | m.p.: 180–185° C. |
| IIb-29 | —C(=O)—OCH₂—C₆H₅ | H | —NO₂ | —COOC₂H₅ | CH₃ | H | H | m.p.: 88–91° C. |
| IIb-30 | —C(=O)—O—CH₃ | H | —NO₂ | —COO—C₄H₉-t | CH₃ | H | H | m.p.: 178–181° C. |

TABLE 2-continued

| Ex. No. | A | $R^{1'}$ | $R^{2'}$ | $R^{3'}$ | $R^{4'}$ | $R^{5'}$ | $R^{6'}$ | Physical constants |
|---|---|---|---|---|---|---|---|---|
| IIb-31 | $-\underset{\underset{O}{\parallel}}{C}-OC(CH_3)_3$ | H | $-NO_2$ | 2,6-dichlorophenyl | $CH_3$ | H | H | m.p.: 180–183° C. |
| IIb-32 | $-\underset{\underset{O}{\parallel}}{C}-OC(CH_3)_3$ | H | $-NO_2$ | 3-nitrophenyl | $C_2H_5$ | H | H | m.p.: 168–174° C. |
| IIb-33 | $-\underset{\underset{O}{\parallel}}{C}-OC(CH_3)_3$ | H | $-NO_2$ | 2-chloro-3-nitrophenyl | $CH_3$ | H | H | m.p.: 171–176° C. |
| IIb-34 | $-\underset{\underset{O}{\parallel}}{C}-OC(CH_3)_3$ | H | $-NO_2$ | 3-nitrophenyl | H | $C_4H_9$-n | H | m.p.: 98–107° C. |
| IIb-35 | $-\underset{\underset{O}{\parallel}}{C}-OC(CH_3)_3$ | H | $-NO_2$ | 4-nitrophenyl | $CH_3$ | H | H | m.p.: 205–206° C. |
| IIb-36 | $-\underset{\underset{O}{\parallel}}{C}-OC(CH_3)_3$ | H | $-NO_2$ | 2-nitrophenyl | $CH_3$ | H | H | m.p.: 145–146° C. |
| IIb-37 | $-\underset{\underset{O}{\parallel}}{C}-OC(CH_3)_3$ | H | $-NO_2$ | $-COOC_2H_5$ | $-CH_2-(CH_2)_2-CH_2-$ | | H | MS: 368 M$^+$ (0.1), 57(100) |

TABLE 2-continued

| Ex. No. | A | $R^{1'}$ | $R^{2'}$ | $R^{3'}$ | $R^{4'}$ | $R^{5'}$ | $R^{6'}$ | Physical constants |
|---|---|---|---|---|---|---|---|---|
| IIb-38 | —C(=O)—OCH$_2$CH=CH$_2$ | H | —NO$_2$ | —COOC$_4$H$_9$-t | H | H | H | m.p.: 123–124° C. |
| IIb-39 | —C(=O)—OCH$_2$CH=CH$_2$ | H | —NO$_2$ | —COOC$_4$H$_9$-t | CH$_3$ | H | H | m.p.: 120–126° C. |
| IIb-40 | —C(=O)—OC(CH$_3$)$_3$ | H | | 2,5-dichloro-4-isopropoxyphenyl-N(C=O—)$_2$ | CH$_3$ | H | H | m.p.: 186–191° C. |
| IIb-41 | —C(=O)—OC(CH$_3$)$_3$ | H | | 2,5-dichloro-4-isopropoxyphenyl-N(C=O—)$_2$ | phenyl | H | H | m.p.: 204–205° C. |
| IIb-42 | —C(=O)—OC(CH$_3$)$_3$ | H | | —O(C=O—)$_2$ | phenyl | H | H | m.p.: 182–184° C. |
| IIb-43 | —C(=O)—OC(CH$_3$)$_3$ | H | | phenyl-N(C=O—)$_2$ | H | H | H | m.p.: 88–93° C. |
| IIb-44 | —C(=O)—OC(CH$_3$)$_3$ | H | | phenyl-N(C=O—)$_2$ | phenyl | H | H | m.p.: 45–51° C. |

TABLE 2-continued

| Ex. No. | A | R¹' | R²' | R³' | R⁴' | R⁵' | R⁶' | Physical constants |
|---|---|---|---|---|---|---|---|---|
| IIb-45 | —C(=O)—OC(CH₃)₃ | H | H | —N(C(=O)—)(C(=O)—) phenyl (phthalimido) | CH₃ | H | H | m.p.: 132–135° C. |
| IIb-46 | —C(=O)—OC(CH₃)₃ | H | NO₂ | —COO—C₄H₉-t | CH₃ | H | H | m.p.: 197–199° C. |
| IIb-47 | —C(=O)—OC(CH₃)₃ | H | NO₂ | 4-Cl-C₆H₄ | CH₃ | H | H | m.p.: 165–168° C. |
| IIb-48 | —C(=O)—OC(CH₃)₃ | H | NO₂ | C₆H₅ | CH₃ | H | H | m.p.: 168–172° C. |
| IIb-49 | —C(=O)—OC(CH₃)₃ | H | NO₂ | —COOC₂H₅ | CH₃ | H | H | m.p.: 130–135° C. |
| IIb-50 | —C(=O)—OC(CH₃)₃ | H | NO₂ | —COO—C₄H₉-t | CH₃ | H | H | m.p.: 180–185° C. |
| IIb-51 | —C(=O)—OC(CH₃)₃ | H | NO₂ | —COO—C₄H₉-t | H | H | H | m.p.: 165–168° C. |
| IIb-52 | —C(=O)—OC(CH₃)₃ | H | CHO | CH₃ | H | H | H | ¹H-NMR*)(CDCl₃, 200 MHz) $\delta$=0.95–1.25(4 isomer, 3H), 1.42(s, 9H), 5.55–5.90 (m, 2H), 9.60–9.85(4 isomer, 1H) |
| IIb-53 | —C(=O)—OC(CH₃)₃ | H | CHO | H | H | H | H | IR(CH₂Cl₂): 3300, 2950, 2710, 1700 cm⁻¹ |

TABLE 2-continued

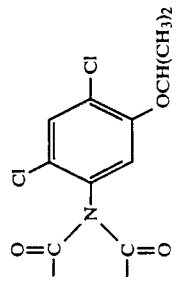

| Ex. No. | A | R¹' | R²' | R³' | R⁴' | R⁵' | R⁶' | Physical constants |
|---|---|---|---|---|---|---|---|---|
| IIb-54 | —C(=O)—OC(CH₃)₃ | H | CHO | H | CH₃ | H | H | IR(CH₂Cl₂): 3400, 2950, 2860, 1720 cm⁻¹ |
| IIb-55 | —C(=O)—OC(CH₃)₃ | F | CHO | H | CH₃ | H | H | MS: 201 [M⁺-isobutene] (5), 183, 153, 127, 83, 57 |
| IIb-56 | —C(=O)—OC(CH₃)₃ | H | —CH=CH—COOH | H | CH₃ | H | H | m.p.: 106–136° C. |
| IIb-57 | —C(=O)—OC(CH₃)₃ | H | —CH=CH—COOH | H | H | H | H | m.p.: 107–130° C. |
| IIb-58 | —C(=O)—OC(CH₃)₃ | H | —CH=CH—COOC₂H₅ | H | H | H | H | m.p.: 59–65° C. |
| IIb-59 | —C(=O)—OC(CH₃)₃ | H | —CH₂OH | H | H | H | H | ¹H-NMR*(CDCl₃, 200 MHz) δ=1.45(9H), 1.65–2.13 (4H), 3.30–3.75(2H), 4.08–4.30(1H), 4.78–4.98(1H), 5.45–5.93(2H) |
| IIb-60 | —C(=O)—OC(CH₃)₃ | H | | | | | H | m.p.: 83° C. |
| IIb-61 | —C(=O)—OC(CH₃)₃ | H | NO₂ | H | H | —CH(CH₃)₂ | H | m.p.: 166–170° C. |
| IIb-62 | —C(=O)—OC(CH₃)₃ | H | COOH | H | H | —CH(CH₃)₂ | H | m.p.: 100–124° C. |
| IIb-63 | —C(=O)—OC(CH₃)₃ | H | COOCH₃ | H | H | —CH(CH₃)₂ | H | m.p.: 85–93° C. |

TABLE 2-continued

| Ex. No. | A | R$^{1'}$ | R$^2$ | R$^{3'}$ | R$^{4'}$ | R$^{5'}$ | R$^{6'}$ | Physical constants |
|---|---|---|---|---|---|---|---|---|
| IIb-64 | —C(=O)—OC(CH$_3$)$_3$ | H | NO$_2$ | 3-methylphenyl with NO$_2$ | C$_3$H$_7$ | H | H | m.p.: 167–181° C. |
| IIb-65 | —C(=O)—OCH$_2$CCl$_3$ | H | NO$_2$ | 2-methyl-1,3-dichlorophenyl | CH$_3$ | H | H | m.p.: 99–100° C. |
| IIb-66 | —C(=O)—OC(CH$_3$)$_3$ | H | —COOC$_2$H$_5$ | H | CH$_3$ | H | H | m.p.: 70–75° C. |
| IIb-67 | —C(=O)—OC(CH$_3$)$_3$ | H | —COOC$_4$H$_9$ | H | CH$_3$ | H | H | m.p.: 65–71° C. |
| IIb-68 | —C(=O)—OC(CH$_3$)$_3$ | H | —C(=O)—N(CH$_3$)$_2$ | H | H | H | H | m.p.: 115–118° C. |
| IIb-69 | —C(=O)—OC(CH$_3$)$_3$ | H | —C(=O)—N(CH$_3$)$_2$ | H | CH$_3$ | H | H | m.p.: 121–124° C. |
| IIb-70 | —C(=O)—OC(CH$_3$)$_3$ | H | —P(=O)(OH)(OCH$_3$) | H | CH$_3$ | H | H | MS [m/e, % rel. Int.]: 305 [M$^+$] (0.9), 249(21), 205 (10), 188(15), 83(100), 57(68) |
| IIb-71 | cyclohexanone with CH$_3$ and CH(CH$_3$)$_2$ substituents | H | —C(=O)—OC(CH$_3$)$_3$ | H | CH$_3$ | H | H | m.p.: 72–78° C. |
| IIb-72 | —C(=O)—OCH$_2$CH$_2$OCH$_3$ | H | —CO$_2$CH$_3$ | H | CH$_3$ | H | H | n$_D^{20}$ 1.4802 |

TABLE 2-continued

| Ex. No. | A | R¹ | R² | R³ | R⁴ | R⁵ | R⁶ | Physical constants |
|---|---|---|---|---|---|---|---|---|
| IIb-73 | —C(=O)—OCH₂CH₂OCH₃ | H | —NO₂ | 3-nitrophenyl | CH₃ | H | H | m.p.: 166-170° C. |
| IIb-74 | —C(=O)—CH₃ | H | —CO₂H | H | CH₃ | H | H | m.p.: 202-220° C. |
| IIb-75 | —C(=O)—(CH₂)₅CH₃ | H | —CO₂H | H | CH₃ | H | H | m.p.: 144-146° C. |
| IIb-76 | —C(=O)—(CH₂)₁₆CH₃ | H | —CO₂H | H | CH₃ | H | H | m.p.: 107° C. |
| IIb-77 | —C(=O)—OC(CH₃)₃ | H | —CO₂CH₂CH(CH₃)₂ | H | CH₃ | H | H | m.p.: 63-64° C. |
| IIb-78 | —C(=O)—OC(CH₃)₃ | H | —CO₂CH₃ | H | —CH(CH₃)₂ | H | H | ¹H-NMR(CDCl₃): δ=0.90 (6H), 1.43(9H); 3.68 (3H); 5.75(2H). |
| IIb-79 | —C(=O)—OC(CH₃)₃ | H | —CO₂CH₃ | H | CH₃ | CH₃ | H | ¹H-NMR(CDCl₃): δ=1.05 (3H), 1.40(9H); 1.68 (3H); 3.67(3H); 5.45 (1H). |
| IIb-80 | —C(=O)—OC(CH₃)₃ | H | —CO₂CH₃ | H | —CH₂CH(CH₃)₂ | phenyl | H | ¹H-NMR(CDCl₃): δ=0.73-0.86(8H), 1.43(9H); 3.68(3H); 5.82(1H); 7.15–7.30(5H). |
| IIb-81 | —C(=O)—OC(CH₃)₃ | H | —CO₂H | H | —CH(CH₃)₂ | H | H | m.p.: 154-158° C. |
| IIb-82 | —C(=O)—OC(CH₃)₃ | H | —CO₂H | H | CH₃ | CH₃ | H | m.p.: 147-152° C. |

TABLE 2-continued

| Ex. No. | A | $R^{1'}$ | $R^{2'}$ | $R^{3'}$ | $R^{4'}$ | $R^{5'}$ | $R^{6'}$ | Physical constants |
|---|---|---|---|---|---|---|---|---|
| IIb-83 | —C(=O)—OC(CH$_3$)$_3$ | H | —CO$_2$H | H | CH$_2$CH(CH$_3$)CH$_3$ |  | H | m.p.: 122–125° C. |
| IIb-84 | —C(=O)—OC(CH$_3$)$_3$ | H | —NO$_2$ |  | CH$_3$ | H | H | m.p.: 169–170° C. |
| IIb-85 | —C(=O)—OC(CH$_3$)$_3$ | H | —CN | H | CH$_2$CH(CH$_3$)$_2$ | CH(CH$_3$)$_2$ | H | m.p.: 117–121° C. |
| IIb-86 | —C(=O)—OC(CH$_3$)$_3$ | H | —CN | H | CH(CH$_3$)$_2$ | C$_6$H$_5$ | H | m.p.: 84–105° C. |
| IIb-87 | —C(=O)—OC(CH$_3$)$_3$ | H | —CO$_2$H | H | CH(CH$_3$)$_2$ | C$_6$H$_5$ | H | m.p.: 151–171° C. (Z) |
| IIb-88 | —C(=O)—OC(CH$_3$)$_3$ | H | —CO$_2$H | H | CH$_2$CH(CH$_3$)$_2$ | CH(CH$_3$)$_2$ | H | m.p.: 150–156° C. |
| IIb-89 | —C(=O)—OC(CH$_3$)$_3$ | H | —CO$_2$H | H |  | H | H | MS: 307 [M$^+$] |

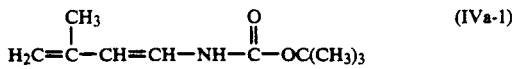

A solution of 56 g (0.5 mol) of trans-4-methyl-2,4-pentadienecarboxylic acid and 80 g (0.62 mol) of N,N-diisopropylethylamine in 300 ml of acetone is treated at −5° C. over the course of 30 minutes with a solution of 54 g (0.5 mol) of ethyl chloroformate in 150 ml of acetone. After a further 30 minutes at 0° C., an ice-cooled solution of 65 g (1 mol) of sodium azide in 150 ml of water is added dropwise. The mixture is stirred at 0° C. for 15 minutes and then worked up using water/toluene. The toluene phase, which is concentrated to about 300 ml, is then added dropwise to a solution of 29.6 g (0.4 mol) of tert-butanol and 250 mg (1.5 mmol) of tert-butylcatechol in 200 ml of toluene which is boiling under reflux. The course of the reaction is monitored by IR spectroscopy. The mixture is allowed to cool to room temperature and is concentrated. After separation by column chromatography using the eluent petroleum ether/ethyl acetate (6:1), 59 g (65 % of theory) of tert-butyl trans-3-methyl-1,3-butadiene-1-carbamate are obtained.

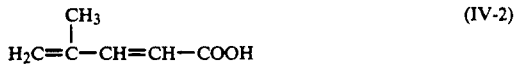

10 g (0.07 mol) of ethyl trans-4-methyl-2,4-pentadienecarboxylate, dissolved in a solvent mixture of 75 ml of methanol, 17 ml of tetrahydrofuran and 2.5 ml of water, are treated at 0° C. with 2.5 g (0.1 mol) of lithium hydroxide and the mixture is stirred at room temperature for 20 hours. After diluting with 200 ml of water, the mixture is extracted once with diethyl ether and the aqueous phase is adjusted to pH 1 at 0° C. using concentrated hydrochloric acid. The mixture is extracted using diethyl ether, the combined organic phases are washed several times with water and saturated sodium chloride solution and 6.1 g (76 % of theory) of trans-4-methyl-2,4-pentadienecarboxylic acid are obtained after drying and concentrating.

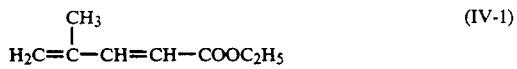

77 g (2.57 mol) of sodium hydride (80 % strength in oil) are added in portions at 0° C under a nitrogen atmosphere to a solution of 630 g (2.8 mol) of triethyl phosphonoacetate in 500 ml of tetrahydrofuran. The cooling bath is removed and the mixture is stirred until evolution of hydrogen is complete (about 30 minutes). A solution of 200 g (2.8 mol) of methacrolein in 2000 ml of tetrahydrofuran is then added dropwise at 0° C. and the mixture is subsequently stirred at 0° C. for 1 hour and at room temperature for 2 hours. For working-up, the mixture is divided, treated with water and extracted several times with ethyl acetate. After drying, concentrating and distilling, 146 g (37 % of theory) of ethyl trans-4-methyl-2,4-pentadienecarboxylate of boiling point 76°–90° C./20 mbar are obtained.

USE EXAMPLE

The compounds according to the invention were tested for in vivo activity in the mouse candidiasis, mouse cryptococcosis and mouse aspergillosis models in the i.v., i.p., s.c. and oral dosage administration modes.

The course of the mouse candidiasis may be described by way of example: Male $CF_1$ SPF mice were infected by injection of the microorganism suspension in physiological NaCl solution (0.2 ml/animal) into the tail vein using $1–3 \times 10^6$ budding cells of C. albicans per animal.

Under these infection conditions, non-treated control animals develop renal candidiasis and 95–100% of the animals employed die of this infection within 6 days p.i. If infected animals are treated orally or parenterally twice daily, beginning with the day of infection, with the compounds according to the invention in doses of $2 \times 5$ to $2 \times 50$ mg/kg of body weight over the course of 2–5 days, >80–100% of the animals survive the infection in good condition.

The C. albicans microorganism counts in the kidneys of the infected and treated animals on the 4th day p.i. are on average 2–3 powers of ten below those of untreated, infected control animals.

Comparable effects can also be achieved in the mouse cryptococcosis and mouse aspergillosis test models.

According to informative investigations of the pharmacokinetics of the compounds according to the invention in mice after oral dosage of 25 mg/kg of body weight, these are rapidly and nearly completely absorbed intestinally. Maximum serum concentrations from 20- >30 mcg/ml result.

The active compounds are eliminated renally within 12 hours post administration. The urine concentrations reach values between 10 and >30 mcg/ml.

The in vivo effects of some compounds are shown by way of example in the mouse candidiasis model in the following table:

| Example No. | Dose oral mg/kg | Number of surviving animals on the 6th day p.i. |
|---|---|---|
| Control | 0 | 1/10 |
| I24 | 2 × 25 | 8/10 |
| I100 | 2 × 25 | 10/10 |
| I87 | 2 × 10 | 10/10 |
| I45 | 2 × 50 | 7/10 |

What we claim is:

1. A method of treating a Candida infection in humans and animals which comprises orally administering to a human or animal so afflicted an amount sufficient to be therapeutically effective against said infection of a substituted 2-cyclohexene derivative of the formula

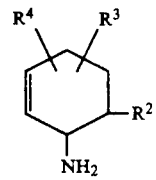

in which $R^2$ represents hydroxy lower alkyl, lower alkoxycarbonyl or phenyl lower alkoxycarbonyl, and $R^3$ and $R^4$ each independently represents hydrogen or lower alkyl.

2. The method according to claim 1, wherein such compound is

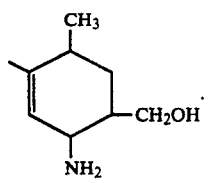
3. The method according to claim 1, wherein such compound is
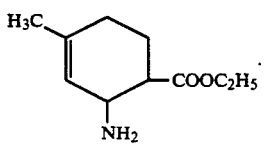
4. The method according to claim 1, wherein such compound is
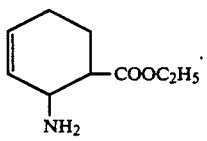
5. The method according to claim 1, wherein such compound is
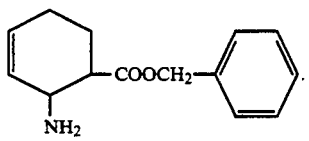
6. The method according to claim 1, wherein such compound is
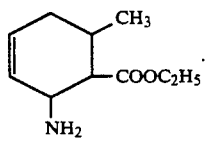
* * * * *

UNITED STATES PATENT AND TRADEMARK OFFICE
CERTIFICATE OF CORRECTION

PATENT NO : 5,296,503
DATED : March 22, 1994
INVENTOR(S): Franz Kunisch, et al.

It is certified that error appears in the above-identified patent and that said Letters Patent is hereby corrected as shown below:

Column 73, lines 13-25, cancel "Claim 3 in its entirety"

Signed and Sealed this

Eighteenth Day of January, 2000

Attest:

Q. TODD DICKINSON

*Attesting Officer*      *Commissioner of Patents and Trademarks*